US008430824B2

(12) United States Patent
Videbaek et al.

(10) Patent No.: US 8,430,824 B2
(45) Date of Patent: Apr. 30, 2013

(54) BIOPSY DRIVER ASSEMBLY HAVING A CONTROL CIRCUIT FOR CONSERVING BATTERY POWER

(75) Inventors: Karsten Videbaek, Jyllinge (DK); Claus Reuber, Roskilde (DK)

(73) Assignee: Bard Peripheral Vascular, Inc., Tempe, AZ (US)

( * ) Notice: Subject to any disclaimer, the term of this patent is extended or adjusted under 35 U.S.C. 154(b) by 529 days.

(21) Appl. No.: 12/608,554

(22) Filed: Oct. 29, 2009

(65) Prior Publication Data

US 2011/0105945 A1    May 5, 2011

(51) Int. Cl.
*A61B 10/00* (2006.01)

(52) U.S. Cl.
USPC .......................................................... 600/562

(58) Field of Classification Search ........... 600/562–572
See application file for complete search history.

(56) References Cited

U.S. PATENT DOCUMENTS

| | | | |
|---|---|---|---|
| 737,293 A | 8/1903 | Summerfeldt |
| 1,585,934 A | 5/1926 | Muir |
| 1,663,761 A | 3/1928 | Johnson |
| 2,953,934 A | 9/1960 | Sundt |
| 3,019,733 A | 2/1962 | Braid |
| 3,224,434 A | 12/1965 | Molomut et al. |
| 3,477,423 A | 11/1969 | Griffith |
| 3,512,519 A | 5/1970 | Hall |
| 3,561,429 A | 2/1971 | Jewett et al. |
| 3,565,074 A | 2/1971 | Foti |
| 3,606,878 A | 9/1971 | Kellogg |
| 3,727,602 A | 4/1973 | Hyden et al. |
| 3,732,858 A | 5/1973 | Banko |
| 3,800,783 A | 4/1974 | Jamshidi |
| 3,844,272 A | 10/1974 | Banko |
| 3,882,849 A | 5/1975 | Jamshidi |
| 4,275,730 A | 6/1981 | Hussein |
| 4,282,884 A | 8/1981 | Boebel |
| 4,306,570 A | 12/1981 | Matthews |
| 4,354,092 A | 10/1982 | Manabe et al. |
| 4,445,509 A | 5/1984 | Auth |
| 4,490,137 A | 12/1984 | Moukheibir |
| 4,549,554 A | 10/1985 | Markham |
| 4,577,629 A | 3/1986 | Martinez |
| 4,589,414 A | 5/1986 | Yoshida et al. |
| 4,603,694 A | 8/1986 | Wheeler |

(Continued)

FOREIGN PATENT DOCUMENTS

| DE | 3924291 A1 | 1/1991 |
|---|---|---|
| DE | 4041614 C1 | 10/1992 |

(Continued)

*Primary Examiner* — Rene Towa

(57) ABSTRACT

A biopsy driver assembly includes a biopsy driver housing. An electrical assembly is coupled to the biopsy driver housing. The electrical assembly includes at least one electrical drive configured for drivably engaging a biopsy probe assembly. A battery is coupled to the biopsy driver housing. A control circuit is coupled to the biopsy driver housing. The control circuit is electrically coupled to the battery and to the electrical assembly. The control circuit has a motion detector, a timer circuit and a battery dwell circuit. The control circuit is configured to conserve the battery by providing electrical power only to the motion detector after a predetermined time following a last detected physical movement of the biopsy driver assembly and to provide electrical power from the battery also to the electrical assembly when a physical movement of the biopsy driver assembly is detected.

2 Claims, 15 Drawing Sheets

U.S. PATENT DOCUMENTS

| | | | |
|---|---|---|---|
| 4,605,011 A | 8/1986 | Naslund | |
| 4,617,430 A | 10/1986 | Bryant | |
| 4,620,539 A | 11/1986 | Andrews et al. | |
| 4,643,197 A | 2/1987 | Greene et al. | |
| 4,645,153 A | 2/1987 | Granzow et al. | |
| 4,678,459 A | 7/1987 | Onik et al. | |
| 4,696,298 A | 9/1987 | Higgins et al. | |
| 4,702,260 A | 10/1987 | Wang | |
| 4,776,346 A | 10/1988 | Beraha et al. | |
| 4,844,087 A | 7/1989 | Garg | |
| 4,850,354 A | 7/1989 | McGurk-Burleson et al. | |
| 4,893,635 A | 1/1990 | de Groot et al. | |
| 4,907,598 A | 3/1990 | Bauer | |
| RE33,258 E | 7/1990 | Onik et al. | |
| 4,940,061 A | 7/1990 | Terwilliger et al. | |
| 4,952,817 A | 8/1990 | Bolan et al. | |
| 4,958,625 A | 9/1990 | Bates et al. | |
| 4,967,762 A | 11/1990 | DeVries | |
| 4,986,278 A | 1/1991 | Ravid et al. | |
| 4,986,279 A | 1/1991 | O'Neill | |
| 4,989,614 A | 2/1991 | Dejter, Jr. et al. | |
| 5,025,797 A | 6/1991 | Baran | |
| 5,125,413 A | 6/1992 | Baran | |
| 5,138,245 A | 8/1992 | Mattinger et al. | |
| 5,146,921 A | 9/1992 | Terwilliger et al. | |
| 5,158,528 A | 10/1992 | Walker et al. | |
| 5,176,628 A | 1/1993 | Charles et al. | |
| 5,225,763 A | 7/1993 | Krohn et al. | |
| 5,234,000 A | 8/1993 | Hakky et al. | |
| 5,236,334 A | 8/1993 | Bennett | |
| 5,249,583 A | 10/1993 | Mallaby | |
| 5,282,476 A | 2/1994 | Terwilliger | |
| 5,282,477 A | 2/1994 | Bauer | |
| 5,324,306 A | 6/1994 | Makower et al. | |
| 5,334,183 A | 8/1994 | Wuchinich | |
| 5,368,029 A | 11/1994 | Holcombe et al. | |
| 5,368,045 A | 11/1994 | Clement et al. | |
| 5,400,798 A | 3/1995 | Baran | |
| 5,439,474 A | 8/1995 | Li | |
| 5,458,112 A | 10/1995 | Weaver | |
| 5,469,860 A | 11/1995 | De Santis | |
| 5,479,486 A | 12/1995 | Saji | |
| 5,485,917 A | 1/1996 | Early | |
| 5,492,130 A | 2/1996 | Chiou | |
| 5,496,860 A | 3/1996 | Matsumoto et al. | |
| 5,511,556 A | 4/1996 | DeSantis | |
| 5,526,822 A | 6/1996 | Burbank et al. | |
| 5,535,755 A | 7/1996 | Heske | |
| 5,546,957 A | 8/1996 | Heske | |
| 5,554,151 A | 9/1996 | Hinchliffe | |
| 5,560,373 A | 10/1996 | DeSantis | |
| 5,564,436 A | 10/1996 | Hakky et al. | |
| 5,569,284 A | 10/1996 | Young et al. | |
| 5,575,293 A | 11/1996 | Miller et al. | |
| 5,591,170 A | 1/1997 | Spievack et al. | |
| 5,601,585 A | 2/1997 | Banik et al. | |
| 5,602,449 A | 2/1997 | Krause et al. | |
| 5,617,874 A | 4/1997 | Baran | |
| 5,649,547 A | 7/1997 | Ritchart et al. | |
| 5,655,542 A | 8/1997 | Weilandt | |
| 5,655,657 A | 8/1997 | Roshdy | |
| 5,665,101 A | 9/1997 | Becker et al. | |
| 5,669,394 A | 9/1997 | Bergey et al. | |
| 5,699,909 A | 12/1997 | Foster | |
| 5,700,265 A | 12/1997 | Romano | |
| 5,709,697 A | 1/1998 | Ratcliff et al. | |
| 5,720,760 A | 2/1998 | Becker et al. | |
| 5,735,264 A | 4/1998 | Siczek et al. | |
| 5,752,923 A | 5/1998 | Terwilliger | |
| 5,755,714 A | 5/1998 | Murphy-Chutorian | |
| 5,766,135 A | 6/1998 | Terwilliger | |
| 5,769,086 A | 6/1998 | Ritchart et al. | |
| 5,769,795 A | 6/1998 | Terwilliger | |
| 5,775,333 A | 7/1998 | Burbank et al. | |
| 5,788,651 A | 8/1998 | Weilandt | |
| 5,792,167 A | 8/1998 | Kablik et al. | |
| 5,807,282 A | 9/1998 | Fowler | |
| 5,817,033 A | 10/1998 | DeSantis et al. | |
| 5,817,034 A | 10/1998 | Milliman et al. | |
| 5,823,970 A | 10/1998 | Terwilliger | |
| 5,827,305 A | 10/1998 | Gordon | |
| 5,830,219 A | 11/1998 | Bird et al. | |
| D403,405 S | 12/1998 | Terwilliger | |
| 5,857,982 A | 1/1999 | Milliman et al. | |
| 5,879,365 A | 3/1999 | Whitfield et al. | |
| 5,908,233 A | 6/1999 | Heskett et al. | |
| 5,913,857 A | 6/1999 | Ritchart et al. | |
| 5,916,198 A | 6/1999 | Dillow | |
| 5,916,229 A | 6/1999 | Evans | |
| 5,928,164 A | 7/1999 | Burbank et al. | |
| 5,944,673 A | 8/1999 | Gregoire et al. | |
| 5,951,490 A | 9/1999 | Fowler | |
| 5,951,575 A | 9/1999 | Bolduc et al. | |
| 5,964,716 A | 10/1999 | Gregoire et al. | |
| 5,971,939 A | 10/1999 | DeSantis et al. | |
| 5,976,164 A | 11/1999 | Bencini et al. | |
| 5,980,469 A | 11/1999 | Burbank et al. | |
| 5,980,545 A | 11/1999 | Pacala et al. | |
| 6,007,495 A | 12/1999 | Matula | |
| 6,007,497 A | 12/1999 | Huitema | |
| 6,007,556 A | 12/1999 | Kablik et al. | |
| 6,017,316 A | 1/2000 | Ritchart et al. | |
| 6,018,227 A | 1/2000 | Kumar et al. | |
| 6,019,733 A | 2/2000 | Farascioni | |
| 6,022,324 A | 2/2000 | Skinner | |
| 6,022,325 A | 2/2000 | Siczek et al. | |
| 6,027,458 A | 2/2000 | Janssens | |
| 6,036,657 A | 3/2000 | Milliman et al. | |
| 6,050,955 A | 4/2000 | Bryan et al. | |
| 6,055,870 A | 5/2000 | Jaeger | |
| 6,077,230 A | 6/2000 | Gregoire et al. | |
| 6,083,176 A | 7/2000 | Terwilliger | |
| 6,083,237 A | 7/2000 | Huitema et al. | |
| 6,086,544 A | 7/2000 | Hibner et al. | |
| 6,106,484 A | 8/2000 | Terwilliger | |
| 6,110,129 A | 8/2000 | Terwilliger | |
| 6,120,462 A | 9/2000 | Hibner et al. | |
| 6,123,957 A | 9/2000 | Jernberg | |
| 6,126,617 A | 10/2000 | Weilandt et al. | |
| 6,142,955 A | 11/2000 | Farascioni et al. | |
| 6,162,187 A | 12/2000 | Buzzard et al. | |
| 6,165,136 A | 12/2000 | Nishtala | |
| 6,193,673 B1 | 2/2001 | Viola et al. | |
| 6,196,978 B1 | 3/2001 | Weilandt et al. | |
| 6,213,957 B1 | 4/2001 | Milliman et al. | |
| 6,220,248 B1 | 4/2001 | Voegele et al. | |
| 6,231,522 B1 | 5/2001 | Voegele et al. | |
| 6,241,687 B1 | 6/2001 | Voegele et al. | |
| 6,267,759 B1 | 7/2001 | Quick | |
| 6,273,861 B1 | 8/2001 | Bates et al. | |
| 6,273,862 B1 | 8/2001 | Privitera et al. | |
| 6,280,398 B1 | 8/2001 | Ritchart et al. | |
| 6,283,925 B1 | 9/2001 | Terwilliger | |
| 6,322,523 B2 | 11/2001 | Weilandt et al. | |
| 6,328,701 B1 | 12/2001 | Terwilliger | |
| 6,331,166 B1 | 12/2001 | Burbank et al. | |
| 6,358,217 B1 | 3/2002 | Bourassa | |
| 6,402,701 B1 | 6/2002 | Kaplan et al. | |
| 6,419,641 B1 | 7/2002 | Mark et al. | |
| 6,428,486 B2 | 8/2002 | Ritchart et al. | |
| 6,428,487 B1 | 8/2002 | Burdorff et al. | |
| 6,432,064 B1 | 8/2002 | Hibner et al. | |
| 6,432,065 B1 | 8/2002 | Burdorff et al. | |
| 6,434,507 B1 * | 8/2002 | Clayton et al. | 702/152 |
| 6,436,054 B1 | 8/2002 | Viola et al. | |
| 6,482,158 B2 | 11/2002 | Mault | |
| 6,485,436 B1 | 11/2002 | Truckai et al. | |
| 6,488,636 B2 | 12/2002 | Bryan et al. | |
| 6,527,736 B1 | 3/2003 | Attinger et al. | |
| 6,540,694 B1 | 4/2003 | Van Bladel et al. | |
| 6,540,761 B2 | 4/2003 | Houser | |
| 6,551,255 B2 | 4/2003 | Van Bladel et al. | |
| 6,554,779 B2 | 4/2003 | Viola et al. | |
| 6,585,664 B2 | 7/2003 | Burdorff et al. | |
| 6,585,694 B1 | 7/2003 | Smith et al. | |
| 6,638,235 B2 | 10/2003 | Miller et al. | |
| 6,656,133 B2 | 12/2003 | Voegele et al. | |

| Patent/Publication | Date | Inventor(s) |
|---|---|---|
| 6,659,105 B2 | 12/2003 | Burbank et al. |
| 6,659,338 B1 | 12/2003 | Dittmann et al. |
| 6,683,439 B2 | 1/2004 | Takano et al. |
| 6,689,072 B2 | 2/2004 | Kaplan et al. |
| 6,695,786 B2 | 2/2004 | Wang et al. |
| 6,712,773 B1 | 3/2004 | Viola |
| 6,712,774 B2 | 3/2004 | Voegele et al. |
| 6,752,768 B2 | 6/2004 | Burdorff et al. |
| 6,753,671 B1 | 6/2004 | Harvey |
| 6,758,824 B1 | 7/2004 | Miller et al. |
| 6,764,495 B2 | 7/2004 | Lee et al. |
| 6,832,990 B2 | 12/2004 | Kortenbach et al. |
| 6,849,080 B2 | 2/2005 | Lee et al. |
| 6,908,440 B2 | 6/2005 | Fisher |
| D508,458 S | 8/2005 | Solland et al. |
| 6,926,676 B2 | 8/2005 | Turturro et al. |
| 6,984,213 B2 | 1/2006 | Horner et al. |
| 7,010,332 B1 * | 3/2006 | Irvin et al. .................. 455/575.2 |
| 7,025,732 B2 | 4/2006 | Thompson et al. |
| D525,583 S | 7/2006 | Vu |
| 7,153,274 B2 | 12/2006 | Stephens et al. |
| 7,189,206 B2 | 3/2007 | Quick et al. |
| 7,189,207 B2 | 3/2007 | Viola |
| 7,219,867 B2 | 5/2007 | Kalis et al. |
| 7,226,424 B2 | 6/2007 | Ritchart et al. |
| 7,276,032 B2 | 10/2007 | Hibner |
| 7,328,794 B2 | 2/2008 | Lubs et al. |
| 7,347,829 B2 | 3/2008 | Mark et al. |
| 7,374,544 B2 | 5/2008 | Freeman et al. |
| 7,397,654 B2 | 7/2008 | Mori |
| 7,402,140 B2 | 7/2008 | Spero et al. |
| 7,405,536 B2 | 7/2008 | Watts |
| 7,407,054 B2 | 8/2008 | Seiler et al. |
| 7,432,813 B2 | 10/2008 | Postma |
| 7,452,367 B2 | 11/2008 | Rassman et al. |
| 7,464,040 B2 | 12/2008 | Joao |
| 7,473,232 B2 | 1/2009 | Teague |
| 7,481,775 B2 | 1/2009 | Weikel, Jr. et al. |
| 7,490,048 B2 | 2/2009 | Joao |
| 7,513,877 B2 | 4/2009 | Viola |
| 7,517,321 B2 | 4/2009 | McCullough et al. |
| 7,517,322 B2 | 4/2009 | Weikel, Jr. et al. |
| 7,648,466 B2 | 1/2010 | Stephens et al. |
| 7,670,299 B2 | 3/2010 | Beckman et al. |
| 7,717,861 B2 | 5/2010 | Weikel et al. |
| 7,727,164 B2 | 6/2010 | Cicenas et al. |
| 7,740,594 B2 | 6/2010 | Hibner |
| 7,740,596 B2 | 6/2010 | Hibner |
| 7,740,597 B2 | 6/2010 | Cicenas et al. |
| 7,762,961 B2 | 7/2010 | Heske et al. |
| 7,828,746 B2 | 11/2010 | Teague |
| 7,854,706 B2 | 12/2010 | Hibner |
| 7,883,476 B2 | 2/2011 | Miller et al. |
| 7,974,681 B2 | 7/2011 | Wallace et al. |
| 8,073,008 B2 | 12/2011 | Mehta et al. |
| 8,190,238 B2 | 5/2012 | Moll et al. |
| 2001/0007925 A1 | 7/2001 | Ritchart et al. |
| 2001/0011156 A1 | 8/2001 | Viola et al. |
| 2001/0012919 A1 | 8/2001 | Terwilliger |
| 2001/0014779 A1 | 8/2001 | Burbank et al. |
| 2001/0034530 A1 | 10/2001 | Malackowski et al. |
| 2001/0044595 A1 | 11/2001 | Reydel et al. |
| 2001/0047183 A1 * | 11/2001 | Privitera et al. ............... 606/170 |
| 2002/0065474 A1 | 5/2002 | Viola |
| 2002/0067151 A1 | 6/2002 | Tanishita |
| 2002/0068878 A1 | 6/2002 | Jasonni et al. |
| 2002/0082518 A1 | 6/2002 | Weiss et al. |
| 2002/0107043 A1 | 8/2002 | Adamson et al. |
| 2002/0120212 A1 | 8/2002 | Ritchart et al. |
| 2002/0156395 A1 | 10/2002 | Stephens et al. |
| 2003/0130593 A1 | 7/2003 | Gonzalez |
| 2003/0130677 A1 | 7/2003 | Whitman et al. |
| 2003/0163142 A1 | 8/2003 | Paltieli et al. |
| 2003/0229293 A1 | 12/2003 | Hibner et al. |
| 2003/0233101 A1 | 12/2003 | Lubock et al. |
| 2004/0015079 A1 | 1/2004 | Berger et al. |
| 2004/0019297 A1 | 1/2004 | Angel |
| 2004/0030367 A1 | 2/2004 | Yamaki et al. |
| 2004/0049128 A1 | 3/2004 | Miller et al. |
| 2004/0054299 A1 | 3/2004 | Burdorff et al. |
| 2004/0092992 A1 | 5/2004 | Adams et al. |
| 2004/0186393 A1 | 9/2004 | Leigh et al. |
| 2004/0215103 A1 | 10/2004 | Mueller, Jr. et al. |
| 2004/0220495 A1 | 11/2004 | Cahir et al. |
| 2004/0249278 A1 | 12/2004 | Krause |
| 2004/0267157 A1 | 12/2004 | Miller et al. |
| 2005/0004492 A1 | 1/2005 | Burbank et al. |
| 2005/0004559 A1 | 1/2005 | Quick et al. |
| 2005/0010131 A1 | 1/2005 | Burbank et al. |
| 2005/0020909 A1 | 1/2005 | Moctezuma de la Barrera et al. |
| 2005/0027210 A1 | 2/2005 | Miller |
| 2005/0049489 A1 | 3/2005 | Foerster et al. |
| 2005/0049521 A1 | 3/2005 | Miller et al. |
| 2005/0080355 A1 | 4/2005 | Mark |
| 2005/0085838 A1 | 4/2005 | Thompson et al. |
| 2005/0088120 A1 * | 4/2005 | Avis ............................. 315/360 |
| 2005/0101879 A1 | 5/2005 | Shidham et al. |
| 2005/0113715 A1 | 5/2005 | Schwindt et al. |
| 2005/0113716 A1 | 5/2005 | Mueller, Jr. et al. |
| 2005/0124914 A1 | 6/2005 | Dicarlo et al. |
| 2005/0124915 A1 | 6/2005 | Eggers et al. |
| 2005/0165328 A1 | 7/2005 | Heske et al. |
| 2005/0177117 A1 | 8/2005 | Crocker et al. |
| 2005/0193451 A1 | 9/2005 | Quistgaard et al. |
| 2005/0203439 A1 | 9/2005 | Heske et al. |
| 2005/0209530 A1 | 9/2005 | Pflueger |
| 2005/0275378 A1 | 12/2005 | Canino et al. |
| 2005/0277829 A1 | 12/2005 | Tsonton et al. |
| 2005/0277871 A1 | 12/2005 | Selis |
| 2006/0030784 A1 | 2/2006 | Miller et al. |
| 2006/0074344 A1 | 4/2006 | Hibner |
| 2006/0074345 A1 | 4/2006 | Hibner |
| 2006/0113958 A1 | 6/2006 | Lobert et al. |
| 2006/0116603 A1 | 6/2006 | Shibazaki et al. |
| 2006/0129063 A1 | 6/2006 | Thompson et al. |
| 2006/0173377 A1 | 8/2006 | McCullough et al. |
| 2006/0178666 A1 | 8/2006 | Cosman et al. |
| 2006/0184063 A1 | 8/2006 | Miller |
| 2006/0241515 A1 | 10/2006 | Jones et al. |
| 2006/0258956 A1 | 11/2006 | Haberstich et al. |
| 2007/0016101 A1 | 1/2007 | Feldman et al. |
| 2007/0027407 A1 | 2/2007 | Miller |
| 2007/0032741 A1 | 2/2007 | Hibner et al. |
| 2007/0073326 A1 | 3/2007 | Miller et al. |
| 2007/0090788 A1 | 4/2007 | Hansford et al. |
| 2007/0106176 A1 | 5/2007 | Mark et al. |
| 2007/0118049 A1 | 5/2007 | Viola |
| 2007/0149894 A1 | 6/2007 | Heske et al. |
| 2007/0161925 A1 | 7/2007 | Quick et al. |
| 2007/0167782 A1 | 7/2007 | Callahan et al. |
| 2007/0167943 A1 | 7/2007 | Janssen et al. |
| 2007/0179401 A1 | 8/2007 | Hibner |
| 2007/0213590 A1 | 9/2007 | Squicciarini |
| 2007/0213630 A1 | 9/2007 | Beckman et al. |
| 2007/0213632 A1 | 9/2007 | Okazaki et al. |
| 2007/0219572 A1 | 9/2007 | Deck et al. |
| 2007/0236180 A1 | 10/2007 | Rodgers |
| 2007/0239067 A1 * | 10/2007 | Hibner et al. ................. 600/567 |
| 2007/0255173 A1 | 11/2007 | Hibner |
| 2007/0270710 A1 | 11/2007 | Frass et al. |
| 2007/0276288 A1 | 11/2007 | Khaw |
| 2007/0287933 A1 | 12/2007 | Phan et al. |
| 2007/0293788 A1 | 12/2007 | Entrekin et al. |
| 2008/0004545 A1 | 1/2008 | Garrison |
| 2008/0007217 A1 | 1/2008 | Riley |
| 2008/0015429 A1 | 1/2008 | Tsonton et al. |
| 2008/0021487 A1 | 1/2008 | Heisler |
| 2008/0021488 A1 | 1/2008 | Berberich |
| 2008/0030170 A1 | 2/2008 | Dacquay et al. |
| 2008/0064925 A1 | 3/2008 | Gill et al. |
| 2008/0064984 A1 | 3/2008 | Pflueger |
| 2008/0071193 A1 | 3/2008 | Reuber et al. |
| 2008/0079391 A1 | 4/2008 | Schroeck et al. |
| 2008/0110261 A1 | 5/2008 | Randall et al. |
| 2008/0135443 A1 | 6/2008 | Frojd et al. |
| 2008/0146962 A1 | 6/2008 | Ritchie et al. |
| 2008/0146965 A1 | 6/2008 | Privitera et al. |
| 2008/0154151 A1 | 6/2008 | Ritchart et al. |

| | | |
|---|---|---|
| 2008/0161682 A1 | 7/2008 | Kendrick et al. |
| 2008/0161718 A1 | 7/2008 | Schwindt |
| 2008/0161719 A1 | 7/2008 | Miller et al. |
| 2008/0161720 A1 | 7/2008 | Nicoson et al. |
| 2008/0183099 A1 | 7/2008 | Jorgensen et al. |
| 2008/0195066 A1 | 8/2008 | Speeg et al. |
| 2008/0200833 A1 | 8/2008 | Hardin et al. |
| 2008/0200836 A1 | 8/2008 | Speeg et al. |
| 2008/0208194 A1 | 8/2008 | Bickenbach |
| 2008/0215056 A1 | 9/2008 | Miller et al. |
| 2008/0221443 A1 | 9/2008 | Ritchie et al. |
| 2008/0221444 A1 | 9/2008 | Ritchie et al. |
| 2008/0221478 A1 | 9/2008 | Ritchie et al. |
| 2008/0221479 A1 | 9/2008 | Ritchie et al. |
| 2008/0221480 A1 | 9/2008 | Hibner et al. |
| 2008/0228104 A1 | 9/2008 | Uber et al. |
| 2008/0232604 A1 | 9/2008 | Dufresne et al. |
| 2008/0234715 A1 | 9/2008 | Pesce et al. |
| 2008/0281225 A1 | 11/2008 | Spero et al. |
| 2008/0287826 A1 | 11/2008 | Videbaek et al. |
| 2008/0306406 A1 | 12/2008 | Thompson et al. |
| 2008/0308607 A1 | 12/2008 | Timm et al. |
| 2008/0319341 A1 | 12/2008 | Taylor et al. |
| 2009/0030405 A1 | 1/2009 | Quick et al. |
| 2009/0062624 A1 | 3/2009 | Neville |
| 2009/0082695 A1 | 3/2009 | Whitehead |
| 2009/0125062 A1 | 5/2009 | Arnin |
| 2009/0137927 A1 | 5/2009 | Miller |
| 2009/0171243 A1 | 7/2009 | Hibner et al. |
| 2009/0227893 A1 | 9/2009 | Coonahan et al. |
| 2010/0030020 A1 | 2/2010 | Sanders et al. |
| 2010/0030108 A1 | 2/2010 | Anderson et al. |
| 2010/0063416 A1 | 3/2010 | Cicenas et al. |
| 2010/0106053 A1 | 4/2010 | Videbaek et al. |
| 2010/0152611 A1 | 6/2010 | Parihar et al. |
| 2010/0160820 A1 | 6/2010 | Weikel, Jr. et al. |
| 2010/0210966 A1 | 8/2010 | Videbaek |
| 2010/0292607 A1 | 11/2010 | Moore et al. |
| 2010/0312140 A1 | 12/2010 | Smith et al. |
| 2010/0317995 A1 | 12/2010 | Hibner et al. |
| 2010/0317997 A1 | 12/2010 | Hibner et al. |
| 2010/0317998 A1 | 12/2010 | Hibner et al. |
| 2011/0054350 A1 | 3/2011 | Videbaek |
| 2011/0077551 A1 | 3/2011 | Videbaek |
| 2011/0087131 A1 | 4/2011 | Videbaek |
| 2011/0105946 A1 | 5/2011 | Sorensen et al. |
| 2011/0152715 A1 | 6/2011 | Delap et al. |
| 2011/0160611 A1 | 6/2011 | Ritchart et al. |

FOREIGN PATENT DOCUMENTS

| | | |
|---|---|---|
| DE | 10034297 A1 | 4/2001 |
| DE | 10026303 A1 | 2/2002 |
| DE | 20209525 U1 | 11/2002 |
| DE | 10235480 A1 | 2/2004 |
| EP | 0433717 A1 | 6/1991 |
| EP | 0890339 A1 | 1/1999 |
| EP | 0995400 A1 | 4/2000 |
| EP | 1074271 A2 | 2/2001 |
| EP | 1520518 A2 | 4/2005 |
| EP | 1579809 A1 | 9/2005 |
| EP | 1665989 A2 | 6/2006 |
| EP | 2095772 A1 | 9/2009 |
| EP | 2106750 A2 | 10/2009 |
| FR | 1345429 A | 12/1963 |
| FR | 2739293 A1 | 4/1997 |
| GB | 2018601 A | 10/1979 |
| JP | H10508504 A | 8/1998 |
| JP | 2005530554 A | 10/2005 |
| JP | 2006509545 A | 3/2006 |
| JP | 2006528907 A | 12/2006 |
| JP | 2007502159 A | 2/2007 |
| WO | 9508945 A2 | 4/1995 |
| WO | 9624289 A2 | 8/1996 |
| WO | 9628097 A1 | 9/1996 |
| WO | 9825522 A1 | 6/1998 |
| WO | 9831285 A1 | 7/1998 |
| WO | 9835615 A1 | 8/1998 |
| WO | 9846290 A1 | 10/1998 |
| WO | 9933501 A1 | 7/1999 |
| WO | 0004832 A1 | 2/2000 |
| WO | 0030546 A1 | 6/2000 |
| WO | 0059378 A2 | 10/2000 |
| WO | 0172230 A1 | 10/2001 |
| WO | 0222023 A1 | 3/2002 |
| WO | 0232318 A1 | 4/2002 |
| WO | 02069808 A2 | 9/2002 |
| WO | 2005013830 A1 | 2/2005 |
| WO | 2006015302 A1 | 2/2006 |
| WO | 2007047128 A1 | 4/2007 |
| WO | 2007095330 A2 | 8/2007 |
| WO | 2007112751 A2 | 10/2007 |
| WO | 2008021687 A1 | 2/2008 |
| WO | 2008024684 A2 | 2/2008 |
| WO | 2008040812 A1 | 4/2008 |
| WO | 2008131362 A2 | 10/2008 |
| WO | 2010107424 A1 | 9/2010 |
| WO | 2010120294 A1 | 10/2010 |
| WO | 2011019343 A1 | 2/2011 |

* cited by examiner

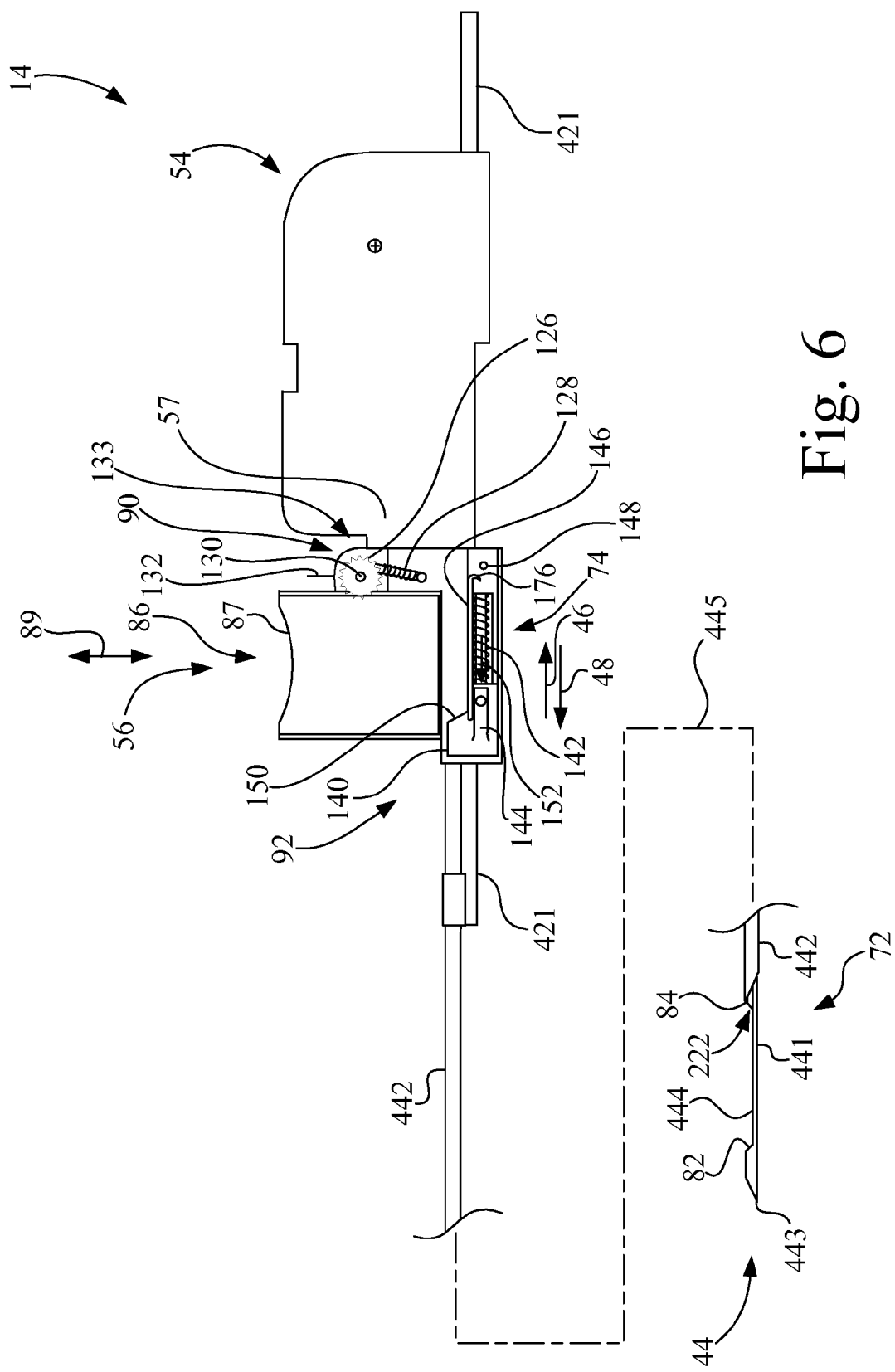

BIOPSY DRIVER ASSEMBLY HAVING A CONTROL CIRCUIT FOR CONSERVING BATTERY POWER

CROSS-REFERENCE TO RELATED APPLICATIONS

This application is related to International Application No. PCT/US2009/040663, filed Apr. 15, 2009, and U.S. patent application Ser. No. 12/551,819 filed Sep. 1, 2009.

MICROFICHE APPENDIX

None.

GOVERNMENT RIGHTS IN PATENT

None.

BACKGROUND OF THE INVENTION

1. Field of the Invention

The present invention relates to a biopsy apparatus, and, more particularly, to a biopsy driver assembly having a control circuit for conserving battery power.

2. Description of the Related Art

A biopsy may be performed on a patient to help in determining whether the cells in a biopsied region are cancerous. One type of vacuum assisted biopsy apparatus includes a hand-held driver assembly having a vacuum source, and a disposable biopsy probe assembly configured for releasable attachment to the driver assembly. One biopsy technique used to evaluate breast tissue, for example, involves inserting a biopsy probe into the breast tissue region of interest to capture one or more tissue samples from the region.

The biopsy probe typically includes a biopsy cannula, e.g., a needle, having a cylindrical side wall defining a lumen, and having a side sample notch located near the distal end that extends though the side wall to the lumen. A cutting cannula is positioned coaxial with the biopsy cannula to selectively open and close the sample notch. Vacuum is applied to the lumen, and in turn to the sample notch, for receiving the tissue to be sampled when the sample notch is opened, after which the sample notch is closed by the cutting cannula to sever the tissue, and the severed tissue is transported by vacuum out of the lumen and collected.

One such hand-held driver assembly is battery powered. The hand-held driver assembly is turned on at the beginning of a procedure, and remains on for the duration of the procedure and/or until a user intervenes to turn off the hand-held driver assembly. Since such a hand-held driver assembly may be used in prolonged sessions, it is important for the power consumption to be held to a minimum to prolong battery life and prevent malfunctions due to lack of battery power.

SUMMARY OF THE INVENTION

The present invention provides a biopsy driver assembly having a control circuit for conserving battery power. The biopsy driver assembly is configured to mount a biopsy probe assembly.

As used herein, the terms "first" and "second" preceding an element name, e.g., first electrical drive, second electrical drive, etc., are for identification purposes to distinguish between different elements having similar characteristic, and are not intended to necessarily imply order, unless otherwise specified, nor are the terms "first", "second", etc., intended to preclude the inclusion of additional similar elements.

The invention, in one form thereof, is directed to a biopsy driver assembly configured to mount a biopsy probe assembly. The biopsy driver assembly includes a biopsy driver housing. An electrical assembly is coupled to the biopsy driver housing. The electrical assembly includes at least one electrical drive configured for drivably engaging the biopsy probe assembly. A battery is coupled to the biopsy driver housing. A control circuit is coupled to the biopsy driver housing. The control circuit is electrically coupled to the battery and to the electrical assembly. The control circuit has a motion detector, a timer circuit and a battery dwell circuit. The control circuit is configured to conserve the battery by providing electrical power only to the motion detector after a predetermined time following a last detected physical movement of the biopsy driver assembly and to provide electrical power from the battery also to the electrical assembly when a physical movement of the biopsy driver assembly is detected.

The invention, in another form thereof, is directed to a biopsy apparatus. The biopsy apparatus includes a biopsy probe assembly and a biopsy driver assembly. The biopsy probe assembly has a sample basket arranged coaxially with a cutter cannula relative to a longitudinal axis. The biopsy probe assembly has a first driven unit coupled to the cutter cannula to facilitate movement of the cutter cannula relative to the longitudinal axis, and has a second driven unit coupled to the sample basket to facilitate movement of the sample basket relative to the longitudinal axis. The biopsy driver assembly is configured to mount the biopsy probe assembly. The biopsy driver assembly includes a biopsy driver housing. An electrical assembly is coupled to the biopsy driver housing. The electrical assembly includes at least one electrical drive configured for drivably engaging the biopsy probe assembly. A battery is coupled to the biopsy driver housing. A control circuit is coupled to the biopsy driver housing. The control circuit is electrically coupled to the battery and to the electrical assembly. The control circuit has a motion detector, a timer circuit and a battery dwell circuit. The control circuit is configured to conserve the battery by providing electrical power only to the motion detector after a predetermined time following a last detected physical movement of the biopsy driver assembly and to provide electrical power from the battery also to the electrical assembly when a physical movement of the biopsy driver assembly is detected.

The invention, in another form thereof, is directed to a biopsy driver assembly configured to mount a biopsy probe assembly. The biopsy driver assembly includes a biopsy driver housing. An electrical assembly is coupled to the biopsy driver housing. The electrical assembly includes at least one electrical drive configured for drivably engaging the biopsy probe assembly. A battery is coupled to the biopsy driver housing. A control circuit is coupled to the biopsy driver housing. The control circuit is electrically coupled to the battery and to the electrical assembly. The control circuit has a motion detector, a timer circuit and a battery dwell circuit. The control circuit is configured to conserve the battery by turning off electrical power to the electrical assembly and to the timer circuit after a predetermined time following a last detected physical movement of the biopsy driver assembly while maintaining electrical power to the motion detector, and configured to provide electrical power from the battery to the motion detector, the timer, and the electrical assembly when a physical movement of the biopsy driver assembly is detected.

The invention, in another form thereof, is directed to a biopsy driver assembly configured to mount a biopsy probe assembly. The biopsy driver assembly includes a biopsy driver housing, and an electrical assembly coupled to the biopsy driver housing. The electrical assembly includes at least one electrical drive configured for drivably engaging the biopsy probe assembly. A control circuit is coupled to the biopsy driver housing. The control circuit is electrically coupled to the electrical assembly. The control circuit has a motion detector, a timer circuit and a power dwell circuit. The power dwell circuit has a power output electrically connected to the electrical assembly. Each of the motion detector and the timer circuit is electrically connected to receive electrical power from the power dwell circuit. The motion detector is communicatively coupled to the timer circuit and to the dwell circuit. The motion detector is configured to provide a first signal to the power dwell circuit to cause the power dwell circuit to enter an operative mode wherein electrical power is supplied to the electrical assembly when the physical movement of the biopsy driver assembly is detected, and the motion detector is configured to provide a second signal to the timer circuit that indicates the last detected physical movement of the biopsy driver assembly. The timer circuit is communicatively coupled to the power dwell circuit. The timer circuit is configured to provide a third signal to the power dwell circuit to cause the power dwell circuit to enter a power dwell mode wherein electrical power is supplied to the motion detector to the exclusion of the timer circuit and the electrical assembly. The third signal is supplied to the power dwell circuit after the predetermined time following the last detected physical movement of the biopsy driver assembly.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein:

FIG. 6 is a side view of the disposable biopsy probe of FIG. 2 showing in further detail a tissue sample retrieval mechanism with the sample collection tank removed;

Corresponding reference characters indicate corresponding parts throughout the several views. The exemplifications set out herein illustrate an embodiment of the invention, and such exemplifications are not to be construed as limiting the scope of the invention in any manner.

DETAILED DESCRIPTION OF THE INVENTION

Figure 1:
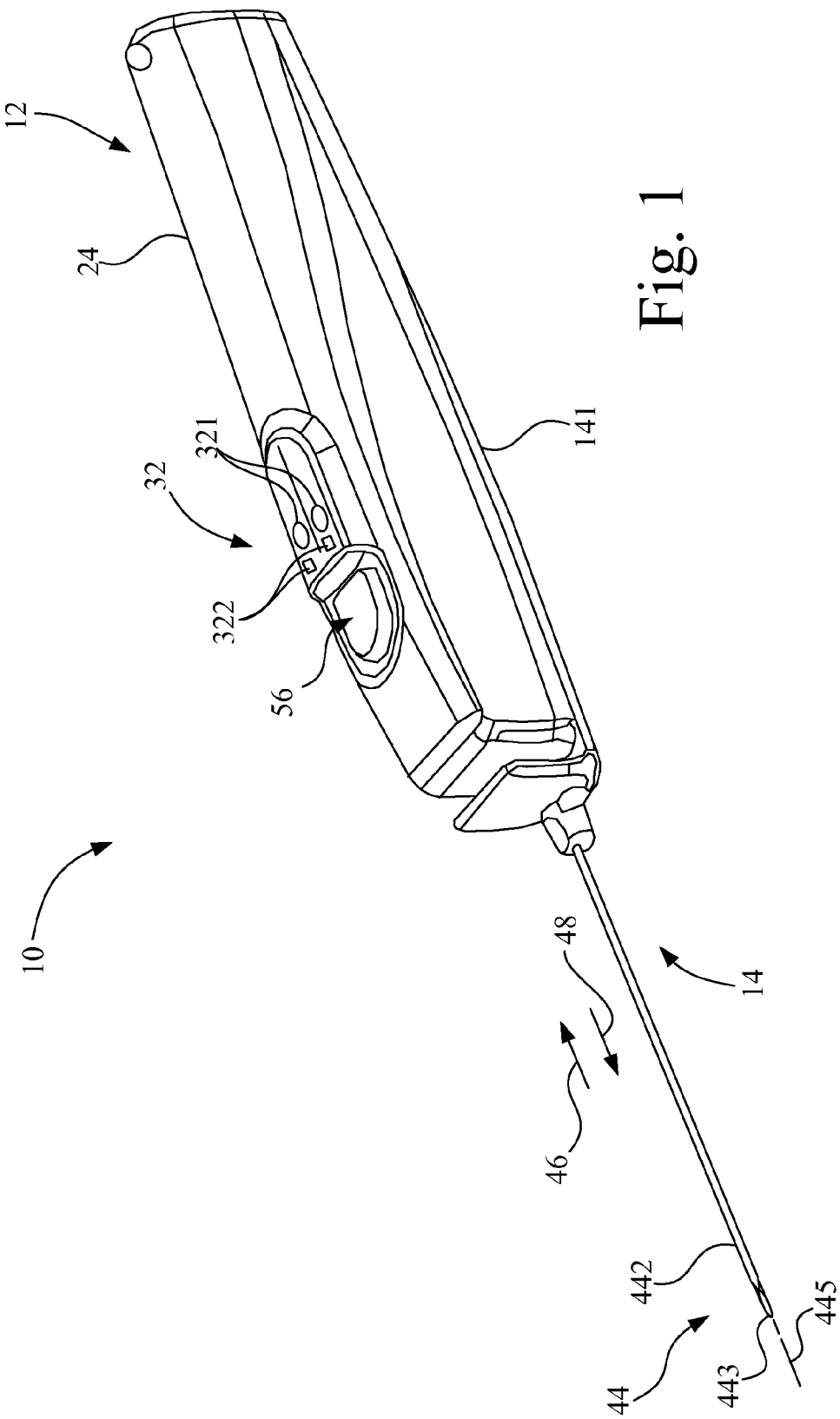
FIG. 1 is a perspective view of a biopsy apparatus, configured in accordance with an embodiment of the present invention, with a disposable biopsy probe mounted to a biopsy driver assembly.
Figure 2:
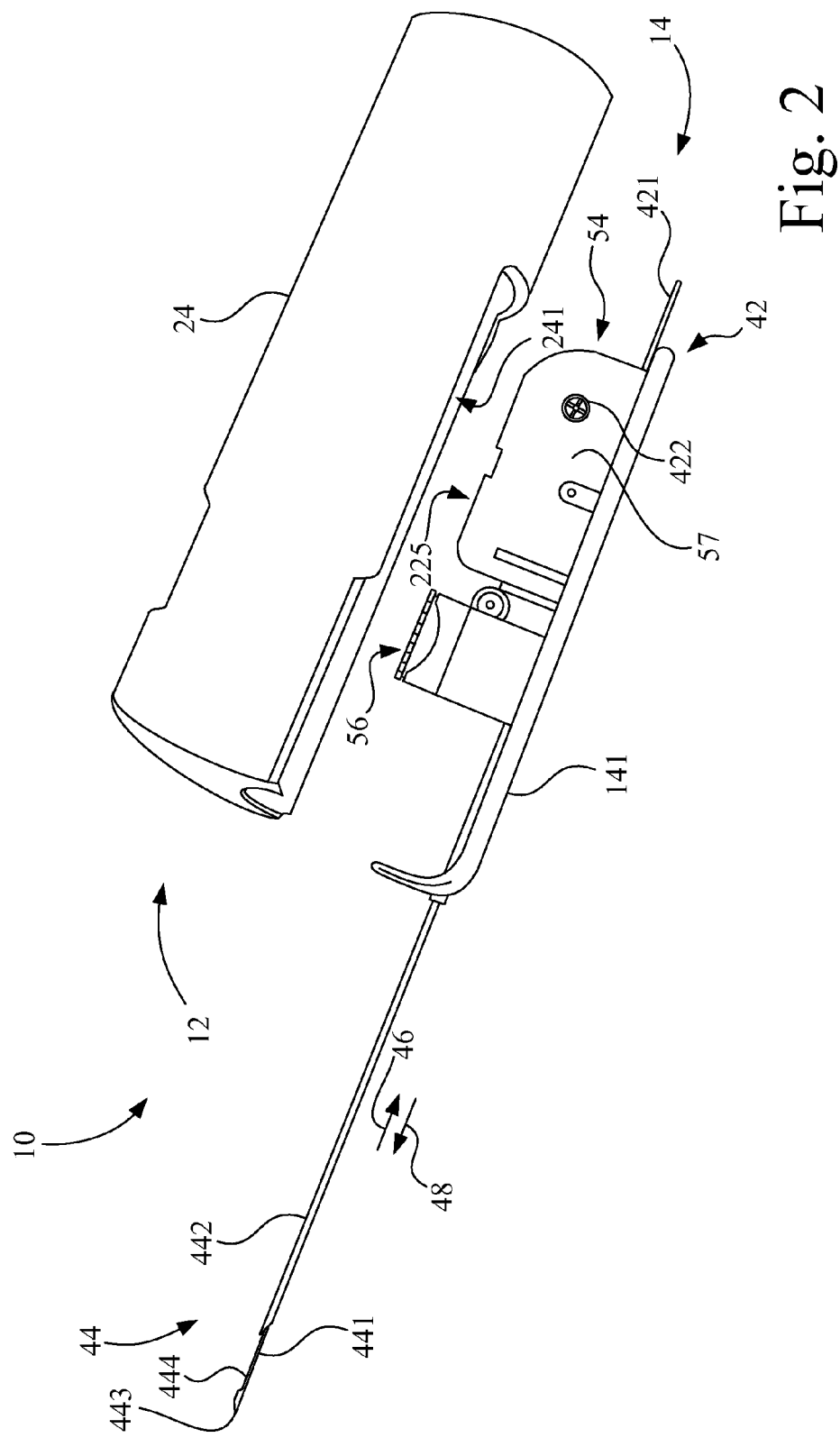
FIG. 2 is a perspective view of a biopsy apparatus of FIG. 1, with the disposable biopsy probe detached from the driver assembly.

Referring now to the drawings, and more particularly to FIGS. 1 and 2, there is shown a biopsy apparatus 10 which generally includes a non-invasive, e.g., non-disposable, biopsy driver assembly 12 and a disposable biopsy probe assembly 14.

Figure 3:
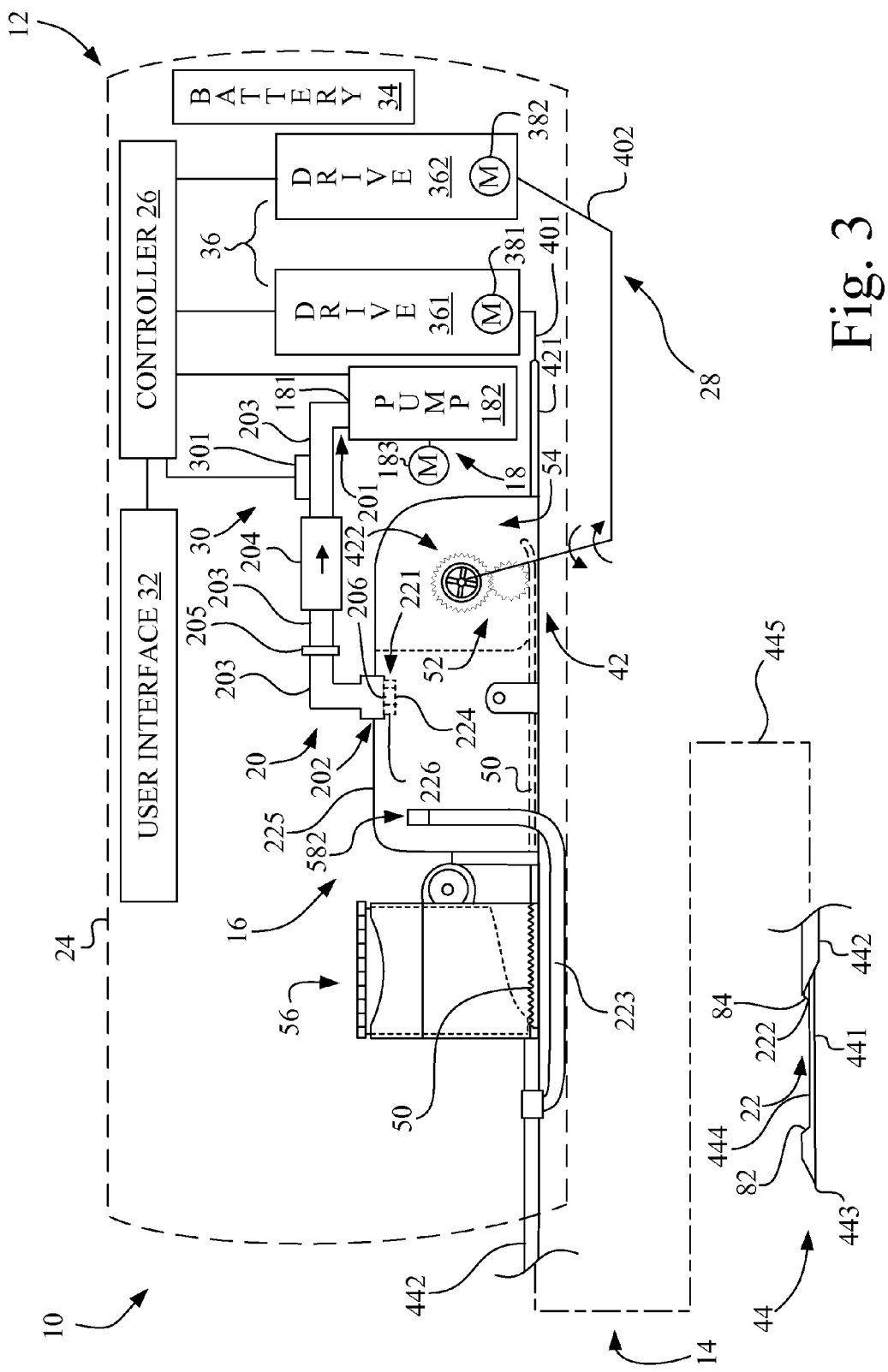
FIG. 3 is a schematic representation of the biopsy apparatus of FIG. 1.

Referring also to FIG. 3, driver assembly 12 and disposable biopsy probe assembly 14 collectively include a fluid management system 16 that includes a vacuum source 18, first vacuum path 20 and a second vacuum path 22. Vacuum source 18 and a first vacuum path 20 are permanently associated with driver assembly 12, and a second vacuum path 22 is permanently associated with disposable biopsy probe assembly 14, as more fully described below, to help facilitate the safe and effective collection of a biopsy tissue sample.

As used herein, the term "non-disposable" is used to refer to a device that is intended for use on multiple patients during the lifetime of the device, and the term "disposable" is used to refer to a device that is intended to be disposed of after use on a single patient. Also, the term "vacuum path" means a fluid passageway used to facilitate a vacuum between two points, the fluid passageway passing through one or more components, such as for example, one or more of tubing, conduits, couplers, and interposed devices. Also, the term "permanently associated" means a connection that is not intended for releasable attachment on a routine basis during the lifetime of the components. Thus, for example, driver assembly 12 including vacuum source 18 and first vacuum path 20 is reusable as a unit in its entirety, whereas disposable biopsy probe assembly 14 and second vacuum path 22 are disposable as a unit in its entirety.

Driver assembly 12 includes a housing 24 configured, and ergonomically designed, to be grasped by a user, and to which the electrical and mechanical components of driver assembly 12 are coupled, i.e., mounted. Driver assembly 12 includes (contained within housing 24) vacuum source 18, first vacuum path 20, a controller 26, an electromechanical power source 28, and a vacuum monitoring mechanism 30. A user interface 32 is located to be mounted to, and externally accessible with respect to, housing 24. Housing 24 defines an elongate cavity 241 which is configured for receiving a corresponding housing 57 of biopsy probe assembly 14 when driver assembly 12 is mounted to biopsy probe assembly 14.

Controller 26 is communicatively coupled to electromechanical power source 28, vacuum source 18, user interface 32, and vacuum monitoring mechanism 30. Controller 26 may include, for example, a microprocessor and associated memory for executing program instructions to perform functions associated with the retrieval of biopsy tissue samples, such as controlling one or more components of vacuum source 18 and electromechanical power source 28. Controller 26 also may execute program instructions to monitor one or more conditions and/or positions of components of biopsy apparatus 10, and to monitor the status of fluid management system 16 associated with driver assembly 12 and biopsy probe assembly 14.

The user interface 32 includes control buttons 321 and visual indicators 322, with control buttons 321 providing user control over various functions of biopsy apparatus 10, and visual indicators 322 providing visual feedback of the status of one or more conditions and/or positions of components of biopsy apparatus 10.

The electromechanical power source 28 may include, for example, an electrical energy source, e.g., battery, 34 and an electrical drive assembly 36. Battery 34 may be, for example, a rechargeable battery. Battery 34 provides electrical power to all electrically powered components in biopsy apparatus 10, and thus for simplicity in the drawings, such electrical couplings are not shown. For example, battery 34 is electrically coupled to vacuum source 18, controller 26, user interface 32 and electrical drive assembly 36.

In the present embodiment, electrical drive assembly 36 includes a first drive 361 and a second drive 362, each being respectively coupled to battery 34, and each of first drive 361 and second drive 362 respectively electrically and controllably coupled to user interface 32.

First drive 361 may include an electrical motor 381 and a motion transfer unit 401 (shown schematically by a line). Second drive 362 may include an electrical motor 382 and a motion transfer unit 402 (shown schematically by a line). Each electrical motor 381, 382 may be, for example, a direct current (DC) motor, stepper motor, etc. Motion transfer unit 401 of first drive 361 may be configured, for example, with a rotational-to-linear motion converter, such as a worm gear arrangement, rack and pinion arrangement, solenoid-slide arrangement, etc. Motion transfer unit 402 of second drive 362 may be configured to transmit rotary motion. Each of first drive 361 and second drive 362 may include one or more of a gear, gear train, belt/pulley arrangement, etc.

Vacuum source 18 is electrically coupled to battery 34, and has a vacuum source port 181 for establishing a vacuum. Vacuum source 18 is electrically and controllably coupled to user interface 32. Vacuum source 18 may further include, for example, a vacuum pump 182 driven by an electric motor 183. Vacuum pump 182 may be, for example, a peristaltic pump, a diaphragm pump, syringe-type pump, etc.

Figure 4A:
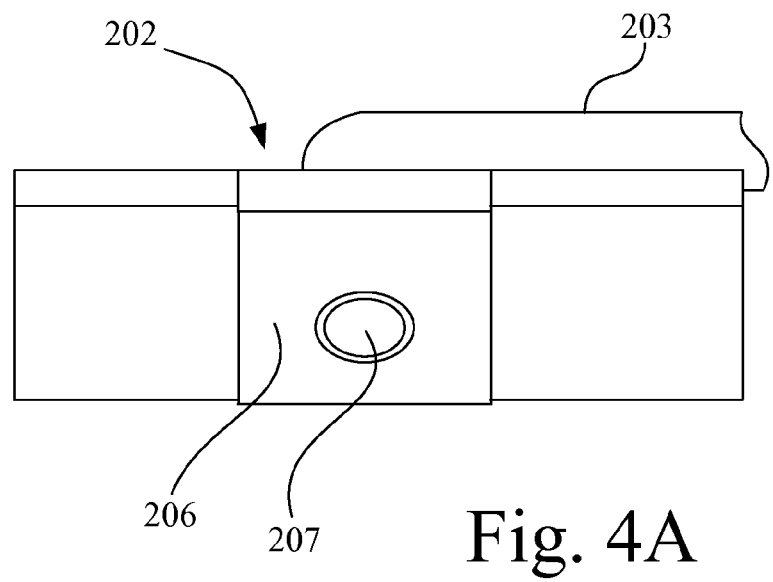
FIG. 4A is a perspective view of a vacuum seal element of the vacuum path of the driver assembly of FIG. 3.

First vacuum path 20 of driver assembly 12 is permanently associated with vacuum source 18. First vacuum path 20, also sometimes referred to as a non-disposable vacuum path, has a proximal end 201 and a distal end 202, and includes, for example, conduits 203, a first one-way valve 204, and a particulate filter 205. Proximal end 201 is fixedly coupled to vacuum source 18 in fluid communication therewith, e.g., is fixedly connected to vacuum source port 181 of vacuum source 18. Referring also to FIG. 4A, distal end 202 includes a first vacuum seal element 206. In the present embodiment, first vacuum seal element 206 is a planar abutment surface that surrounds a first passageway 207 of first vacuum path 20.

First one-way valve 204 is configured and arranged to permit a negative pressure fluid flow toward vacuum source 18 and to prevent a positive pressure fluid flow away from vacuum source 18 toward the distal end 202 of first vacuum path 20. The first one-way valve 204 may be, for example, a check-valve, such as a ball valve or reed valve, that opens with a fluid flow toward vacuum source 18, and closes in the case of a reverse (positive) flow away from vacuum source 18.

In the present embodiment, particulate filter 205 is located between vacuum source 18 and distal end 202 of first vacuum path 20. Particulate filter 205 may be, for example, a mesh screen formed from metal or plastic. However, it is contemplated that particulate filter 205 may be located in fluid management system 16 between vacuum source 18 and a vacuum receiving component of biopsy probe assembly 14.

The vacuum monitoring mechanism 30 is coupled to vacuum source 18 to shut off vacuum source 18 when a sensed vacuum level has fallen below a threshold level. Vacuum monitoring mechanism 30 may include, for example, a vacuum monitor and control program executing on controller 26, and a pressure sensor 301 coupled to controller 26, and in fluid communication with first vacuum path 20 for detecting a pressure in first vacuum path 20. If, for example, the vacuum flow level in first vacuum path 20 falls below a predetermined level, indicating a restriction in fluid management system 16, controller 26 may respond by shutting off vacuum source 18, e.g., turning off electric motor 183. Alternatively, controller 26 may monitor the current supplied to electric motor 183, and if the current exceeds a predetermined amount, indicating a restriction in fluid management system 16, controller 26 may respond by shutting off vacuum source 18, e.g., turning off electric motor 183.

The disposable biopsy probe assembly 14 is configured for releasable attachment to driver assembly 12. As used herein, the term "releasable attachment" means a configuration that facilitates an intended temporary connection followed by selective detachment involving a manipulation of disposable biopsy probe assembly 14 relative to driver assembly 12, without the need for tools.

The disposable biopsy probe assembly 14 includes a cover 141, which essentially serves as a frame, to which a transmission device 42, a biopsy probe 44, housing 57 and the second vacuum path 22 are mounted, with housing 57 being slidably coupled to cover 141. The sliding coupling of housing 57 to cover 141 may be achieved, for example, by a rail and U-bracket configuration. Cover 141 serves as a slidable cover to close elongate cavity 241 in housing 24 of driver assembly 12 to protect the internal structure of driver assembly 12 when biopsy probe assembly 14 is mounted to driver assembly 12. Biopsy probe 44 is drivably coupled to transmission device 42, and transmission device 42 is drivably coupled to electromechanical power source 28 of driver assembly 12 when biopsy probe assembly 14 is mounted to driver assembly 12.

In the embodiment shown, transmission device 42 includes a first driven unit 421 and a second driven unit 422 that are drivably engaged with various components of biopsy probe 44. Also, first driven unit 421 is drivably engaged with first drive 361 of electrical drive assembly 36 of driver assembly 12. Second driven unit 422 is drivably engaged with second drive 362 of electrical drive assembly 36 of driver assembly 12. First driven unit 421 is slidably coupled to housing 57, and second driven unit 422 is contained in housing 57. The sliding coupling of first driven unit 421 (e.g., a sliding member) may be achieved, for example, by placing first driven unit 421 in a longitudinal slide channel formed in housing 57.

In the embodiment shown (see, e.g., FIGS. 1-3), biopsy probe 44 includes a sample basket 441 and a cutter cannula 442. Sample basket 441 has a sharpened tip 443 to aid in puncturing tissue and has a sample notch 444 in the form of a recessed region for receiving a biopsy tissue sample. Sample basket 441 and a cutter cannula 442 are configured to be individually movable along a longitudinal axis 445.

In operation, cutter cannula 442 is linearly driven by first driven unit 421 to traverse over sample notch 444 of sample basket 441 along longitudinal axis 445. For example, first driven unit 421 may be in the form of a linear slide that is drivably engaged with first drive 361 of driver assembly 12, which in turn drives cutter cannula 442 along longitudinal axis 445 in a first direction 46, i.e., toward a proximal end of driver assembly 12, to expose sample notch 444 of sample basket 441, and drives cutter cannula 442 in a second direction 48 opposite to first direction 46 to sever tissue prolapsed into sample notch 444. Also, first driven unit 421 and second driven unit 422 may be configured to operate in unison to advance both sample basket 441 and cutter cannula 442 in unison along an longitudinal axis 445 in a piercing shot operation to aid in inserting biopsy probe 44 into fibrous tissue.

The second driven unit 422 may include a flexible toothed rack 50 and a gear train 52. Flexible toothed rack 50 is connected to sample basket 441, and gear train 52 is engaged with the teeth of flexible toothed rack 50. In operation, second drive 362 transfers rotary motion to gear train 52, and in turn gear train 52 engages flexible toothed rack 50 to move sample basket 441 linearly to transport the tissue captured in sample notch 444 out of the body of the patient. Flexible toothed rack 50 is received in a coiling unit 54 when retracting, thereby enabling substantial reduction in the overall device length of biopsy apparatus 10 as compared to a rigid capture system. Each harvested tissue sample is transported out of the body of the patient and is collected by tissue sample retrieval mechanism 56, which scoops the tissue sample out of sample notch 444.

In the present embodiment, coiling unit 54 and tissue sample retrieval mechanism 56 are as an integral unit with housing 57 that is common to coiling unit 54 and tissue sample retrieval mechanism 56. Housing 57 is attached, e.g., slidably coupled, to cover 141, and contains gear train 52 with at least a portion of flexible toothed rack 50 in engagement with gear train 52. Tissue sample retrieval mechanism 56 will be described in greater detail later. As shown, for example, in FIGS. 2, 5A and 6-8, housing 57 has a distinct shape S1 as a combination of curved and flat surfaces with an overall height H1, length L1, and width W1 dimensions which in combination define a unique profile of housing 57.

In the present embodiment, the second vacuum path 22, also sometimes referred to as a disposable vacuum path 22, has a first end 221 and a second end 222, and includes for example, conduits 223, a second one-way valve 224, and a fluid management tank 225. The first end 221 is configured for removable attachment to the distal end 202 of the first vacuum path 20 of driver assembly 12. The second end 222 is coupled in fluid communication with sample basket 441, and more particularly, is coupled in fluid communication with sample notch 444 of sample basket 441.

Figure 4B:
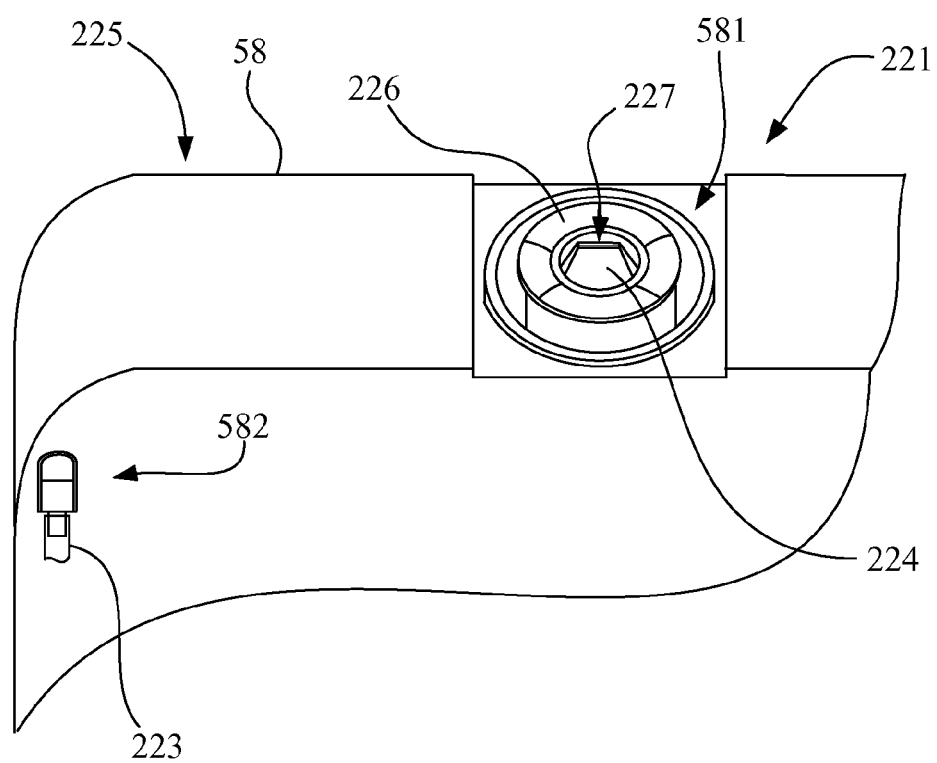
FIG. 4B is a perspective view of a vacuum seal element of the vacuum path of the disposable biopsy probe of FIG. 3.

Referring also to FIG. 4B, the first end 221 of the disposable vacuum path 22 includes a second vacuum seal element 226. The first vacuum seal element 206 of the driver assembly 12 contacts the second vacuum seal element 226 of the disposable biopsy probe assembly 14 in sealing engagement when the disposable biopsy probe assembly 14 is attached to driver assembly 12. The second vacuum seal element 226 is a compliant, e.g., rubber, annular member that surrounds a second passageway 227 of the second vacuum path 22.

The second one-way valve 224 configured and arranged to permit the negative pressure fluid flow from sample basket 441 toward the first end 221 of the second vacuum path 22, and to redundantly (in conjunction with first one-way valve 204 of driver assembly 12) prevent any positive pressure fluid flow in a direction from the first end 221 of the second vacuum path 22 toward sample basket 441. In other words, the second one-way valve 224 provides a redundant second level of protection in preventing any positive pressure from reaching sample notch 444 of sample basket 441. In the present embodiment, the second one-way valve 224 may be, for example, a duckbill valve, e.g., a reed-type valve, that opens with a fluid flow out the bill portion of the duckbill valve, and closes with a reverse flow. As shown, the second one-way valve 224 may be positioned within the second vacuum seal element 226 at first end 221 of second vacuum path 22.

Figure 5A:
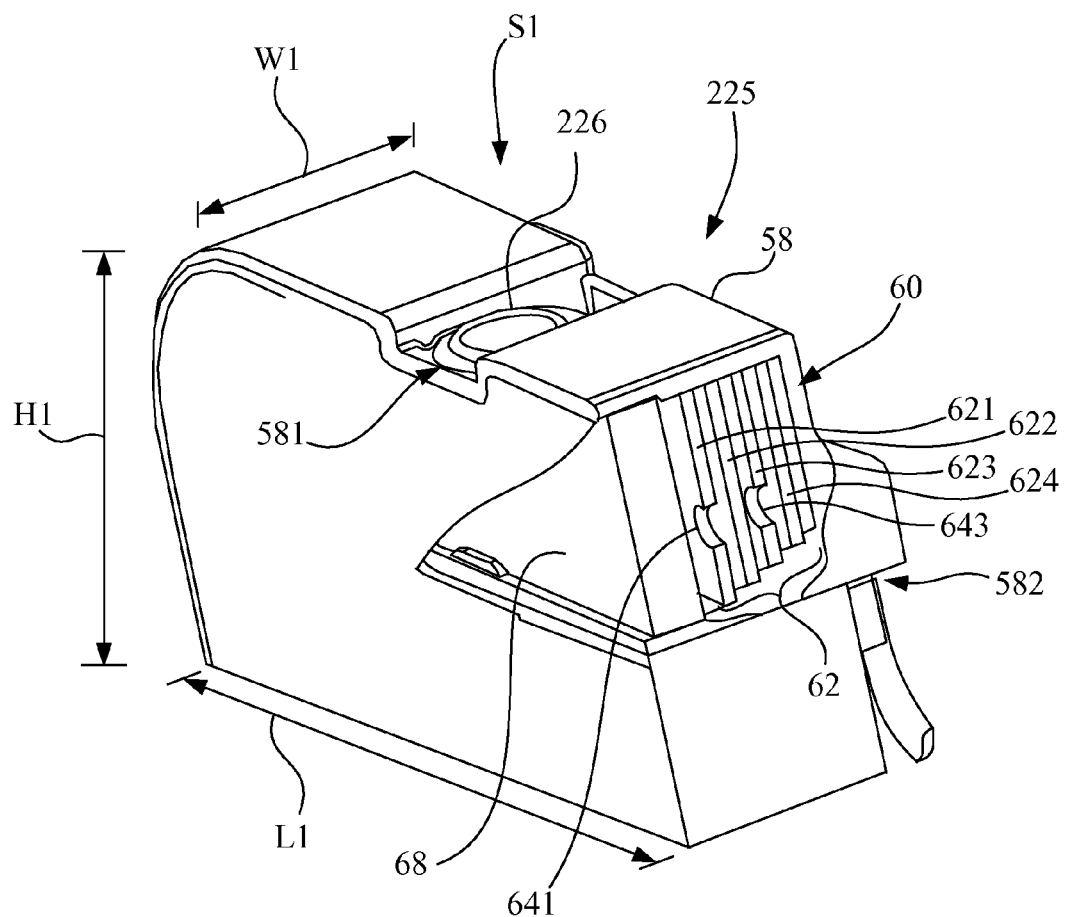
FIG. 5A is a perspective view of the fluid management tank of the disposable biopsy probe shown in FIGS. 2 and 3, with a portion broken away to expose a filter arrangement.

Referring also to FIG. 5A, fluid management tank 225 is fluidically interposed in the second vacuum path 22 between the first end 221 and the second end 222. Fluid management tank 225 includes a body 58 and a filter arrangement 60 contained within body 58 configured to prevent a flow of residual biopsy biological material, e.g., blood and particulate matter, from sample notch 444 of sample basket 441 to vacuum source 18 of driver assembly 12.

Body 58 of fluid management tank 225 has a first port 581 and a second port 582, with the second vacuum path 22 continuing between the first port 581 and the second port 582. The second port 582 of fluid management tank 225 is coupled to sample basket 441. Each of the second one-way valve 224 and the second vacuum seal element 226 of the second vacuum path 22 is coupled to the first port 581 of fluid management tank 225, and in the present embodiment, is mounted to an external surface of body 58 of fluid management tank 225.

Figure 5B:
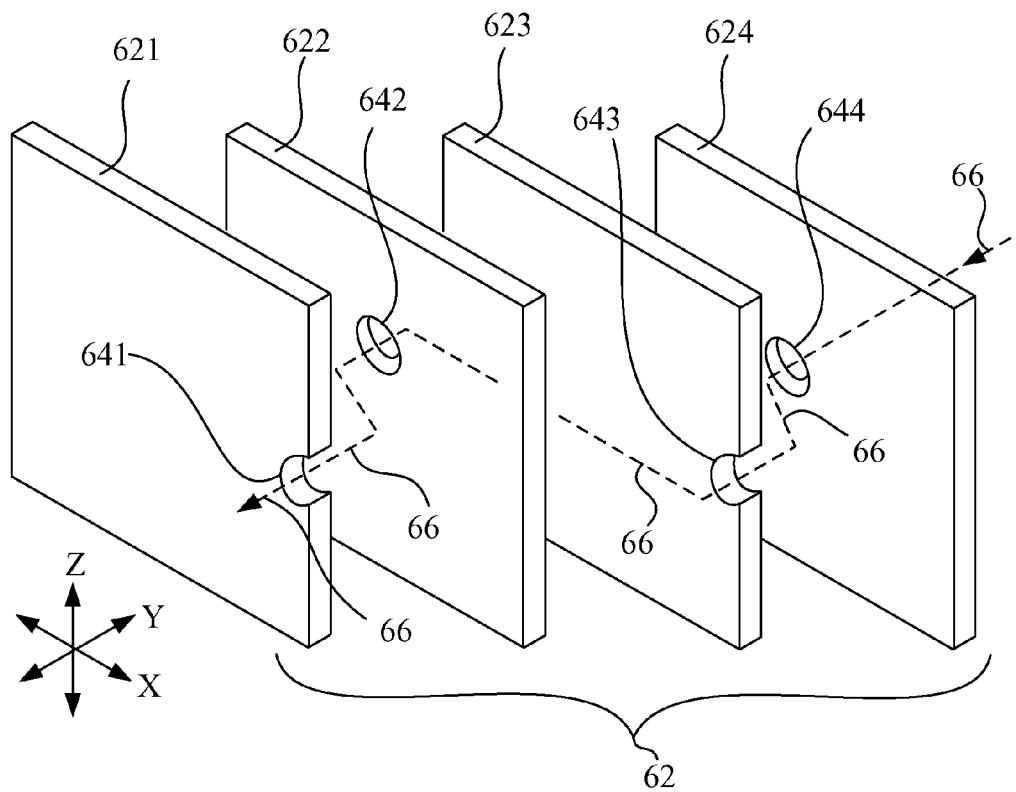
FIG. 5B is an exploded view of a plurality of fluid absorption layers of the filter arrangement of FIG. 5A.

As illustrated in FIGS. 5A and 5B, filter arrangement 60 includes a plurality of fluid absorption layers 62, individually identified as layers 621, 622, 623 and 624, arranged side by side, with each fluid absorption layer 621, 622, 623 and 624 being spaced apart from an adjacent fluid absorption layer e.g., 621 to 622, 622 to 623, 623, to 624. Each fluid absorption layer 621, 622, 623 and 624 has a respective through opening 641, 642, 643, 644, wherein adjacent through openings of through openings 641, 642, 643, 644 of the plurality of fluid absorption layers 62 are offset one to the next, e.g., in at least one of an X, Y, and Z direction, to form a tortuous open fluid passageway 66 through the plurality of fluid absorption layers 62. Each fluid absorption layer 621, 622, 623 and 624 may be, for example, a blotting paper.

Figure 5C:
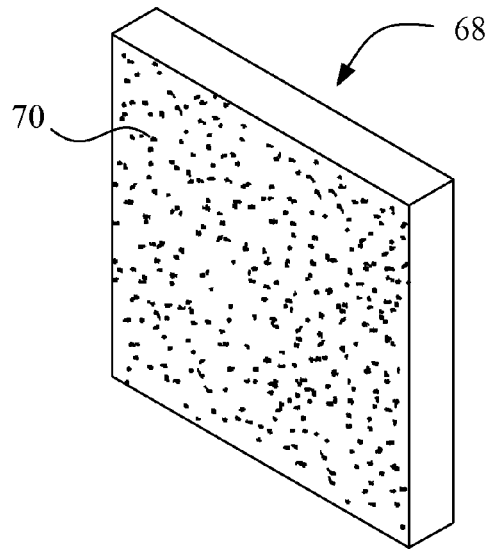
FIG. 5C is a perspective view of a porous filter element of the filter arrangement of FIG. 5A.

As illustrated in FIGS. 5A and 5C, filter arrangement 60 may further include a porous filter element 68 arranged to be fluidically in series with the plurality of fluid absorption layers 62 along the second vacuum path 22 that defines second passageway 227. The porous filter element 68 exhibits increased restriction to fluid flow as an increased number of pores 70 in the porous filter element 68 become clogged by residual biopsy biological material, such as blood and tissue particles. When a volume of the fluid flow through fluid management tank 225 has been reduced to a predetermined level, vacuum monitoring mechanism 30 senses the vacuum restriction, and controller 26 responds to shut off vacuum source 18.

Referring to FIGS. 6-13, each harvested tissue sample is transported out of the body of the patient and is collected by tissue sample retrieval mechanism 56. In general, tissue sample retrieval mechanism 56 collects tissue samples that have been harvested by scooping the tissue sample out of sample notch 444 of sample basket 441 of biopsy probe 44.

Figure 7:
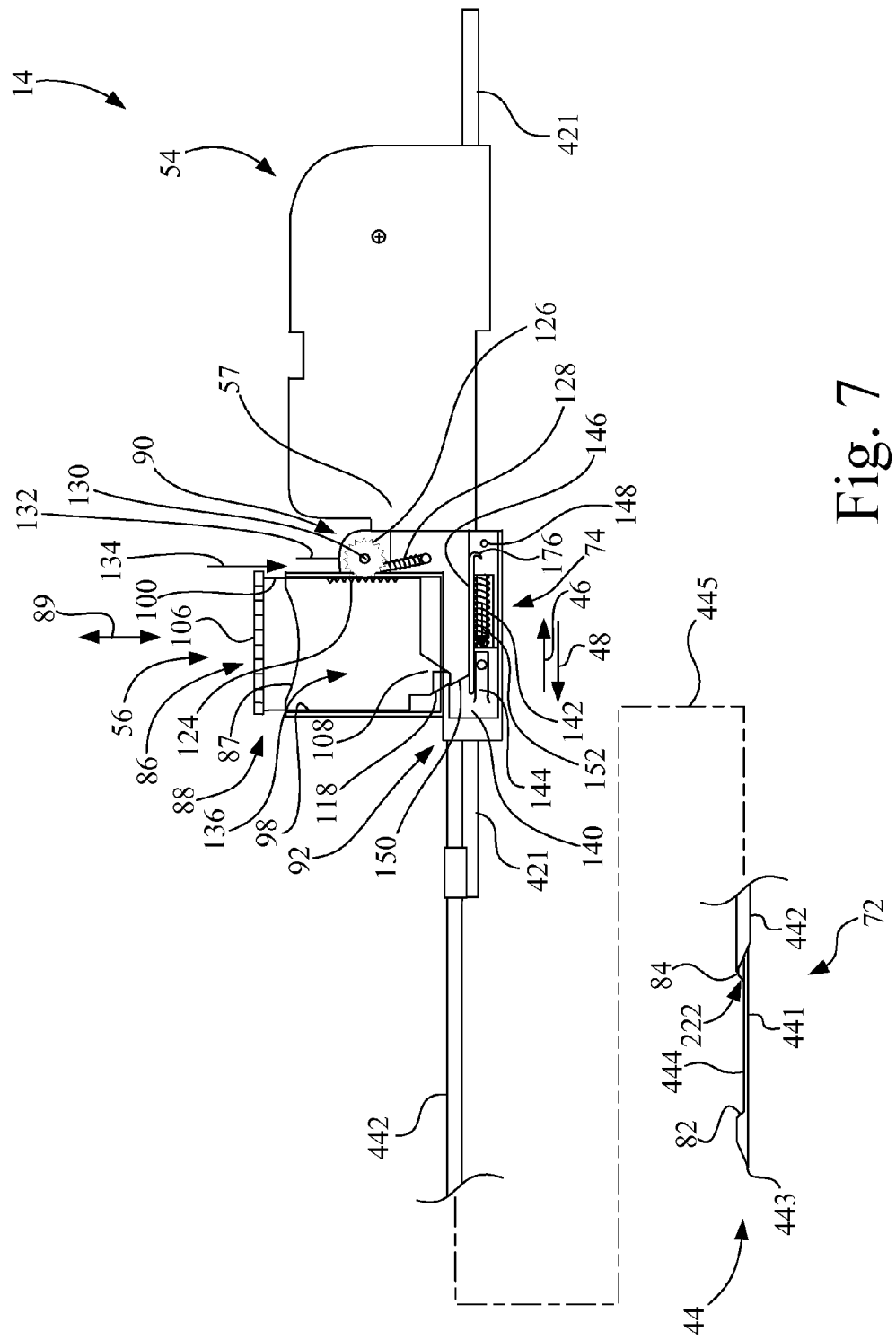
FIG. 7 is a side view of the disposable biopsy probe of FIG. 6 showing the tissue sample retrieval mechanism with the sample collection tank installed, and with the sample collection tank in the raised position.
Figure 8:
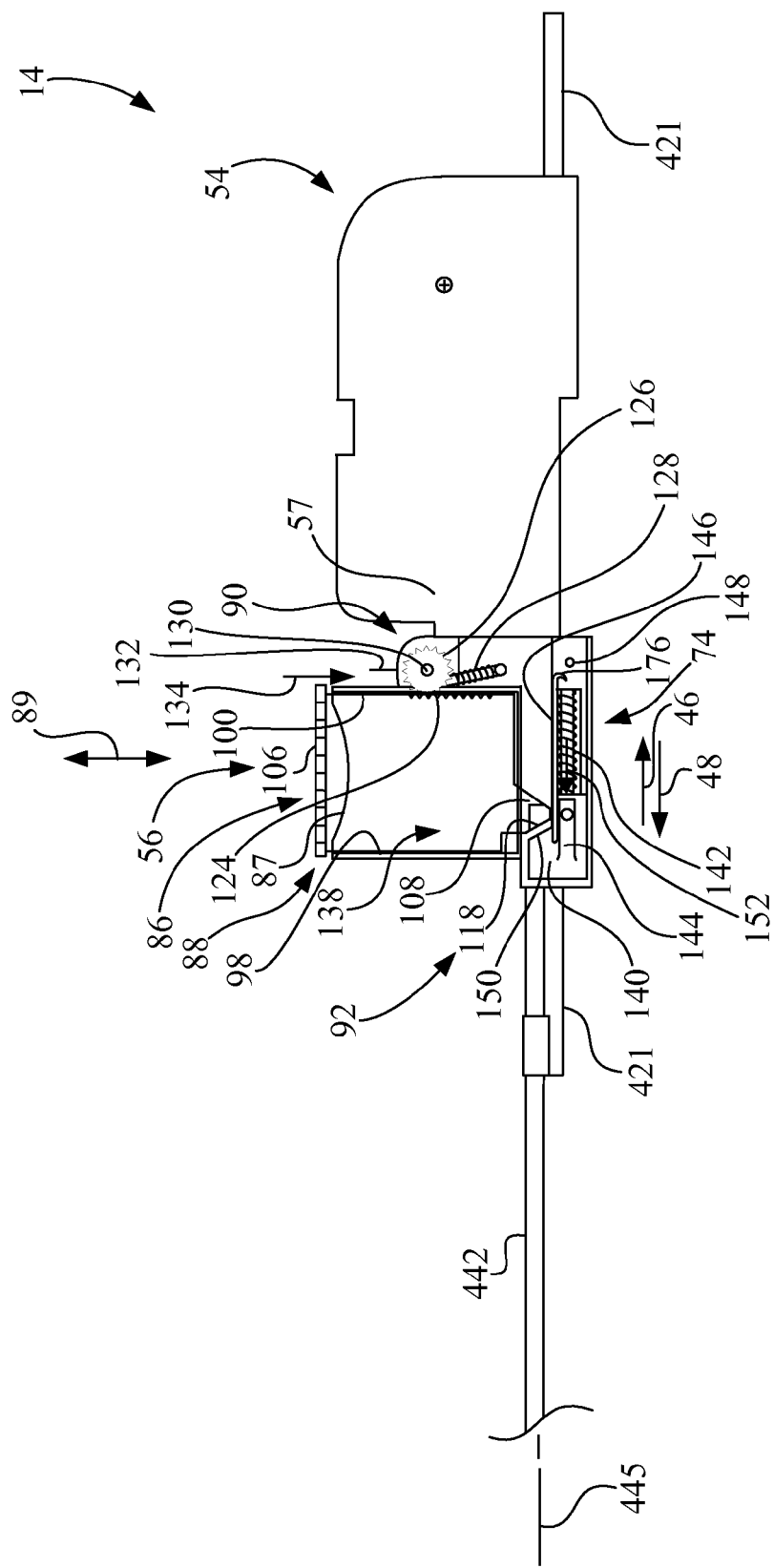
FIG. 8 is a side view of the disposable biopsy probe of FIG. 6 showing the tissue sample retrieval mechanism with the sample collection tank installed, and with the sample collection tank in the lowered collection position.
Figure 12:
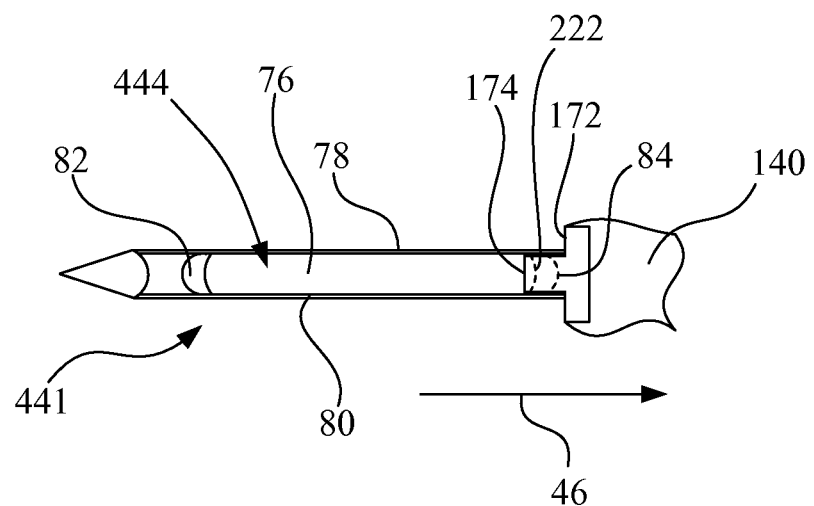
FIG. 12 is a top view of the sample basket and the lift member of the disposable biopsy probe of FIG. 7, with a portion of lift member broken away to expose a T-shaped stop, and a leaf spring tongue forming a portion of the T-shaped stop for removing residual tissue material and debris from a vacuum path at the sample notch of the sample basket.

Referring to FIGS. 6-9, biopsy probe 44 of biopsy probe assembly 14 includes a biopsy cannula, e.g., cutter cannula 442, and sample basket 441 arranged coaxially about longitudinal axis 445. Sample basket 441 having sample notch 444 is movably disposed relative to biopsy (cutter) cannula 442 along longitudinal axis 445 from a tissue harvesting position 72, as shown in FIGS. 6 and 7, to a tissue sample retrieval region 74, as illustrated in FIGS. 6-8 by electromechanical power source 28 and second drive 362, as more fully described above with respect to FIG. 3. Referring also to FIGS. 10 and 12, sample notch 444 is an elongate recessed region of sample basket 441 having a generally semicircular cross-section, and has a recessed floor 76, a pair of spaced elongate edges 78, 80 on opposite sides of recessed floor 76, a leading transition bevel 82, and a trailing transition bevel 84. Leading transition bevel 82 and trailing transition bevel 84 are located at opposite ends of the elongate recessed region, i.e., sample notch, 444.

In the present embodiment, tissue sample retrieval mechanism 56 includes a sample tank receptacle 86, a sample collection tank 88, a toggle mechanism 90, and a tank positioning mechanism 92. Sample collection tank 88 is configured for removable insertion into sample tank receptacle 86.

Sample tank receptacle 86, which may be formed integral with housing 57, includes a hollow guide 87 size to slidably receive sample collection tank 88. Thus, the configuration of sample tank receptacle 86 is such that sample tank receptacle 86 permits bi-directional movement of sample collection tank 88 in directions 89 (signified by double headed arrow) that are substantially perpendicular to longitudinal axis 445. Also, the configuration of sample tank receptacle 86 is such that sample tank receptacle 86 prohibits movement of sample collection tank 88 in a direction 46 or 48 along longitudinal axis 445.

Sample collection tank 88 defines a single collection cavity 94 (see FIG. 9) configured for receiving multiple tissue samples, such as tissue sample TS. Sample collection tank 88 has, in forming collection cavity 94, a base 96, a front wall 98, a rear wall 100, a pair of side walls 102, 104, and a removable cap 106. Sample collection tank 88 further includes a tissue sample scoop 108. Sample collection tank 88 is configured to collect a tissue sample directly from sample notch 444 as sample basket 441 moves along longitudinal axis 445 at tissue sample retrieval region 74. In this regard, tissue sample scoop 108 of sample collection tank 88 is configured to engage sample notch 444 of sample basket 441.

Tissue sample scoop 108 is fixed to and projects downwardly from base 96. Tissue sample scoop 108 extends forward toward a front portion 110 of sample collection tank 88 to terminate at a rim 112. Tissue sample scoop 108 has a tissue collection lumen 114 through which each tissue sample TS harvested by biopsy probe assembly 14 will pass. Tissue collection lumen 114 begins at an opening 116 located near rim 112 and extends to collection cavity 94. Tissue sample scoop 108 has a ramped face 118 located adjacent rim 112. Also, tissue sample scoop 108 has a first shoulder 120 and a second shoulder 122 that are positioned on opposite sides of opening 116.

A rack gear 124 is longitudinally (e.g., vertically) positioned on rear wall 100 of sample collection tank 88 to engage toggle mechanism 90.

Referring to FIGS. 6-9, toggle mechanism 90 is configured to aid in the mounting of sample collection tank 88 in sample tank receptacle 86, and to aid in the removal of sample collection tank 88 from sample tank receptacle 86. Toggle mechanism 90 is mounted to housing 57 and includes a rotary gear 126 and a spring 128. Rotary gear 126 has a rotational axis 130, e.g., an axle, which is attached to, or formed integral with, housing 57. Spring 128 is coupled between rotary gear 126 and housing 57, and is eccentrically mounted to rotary gear 126, i.e., at a location offset from rotational axis 130. Rotary gear 126 is located for driving engagement with rack gear 124 of sample collection tank 88, as sample collection tank 88 is slidably received by sample tank receptacle 86.

Referring to FIGS. 6-8, toggle mechanism 90 is configured to define a break-over point 132, e.g., at the 12:00 o'clock position in the orientation as shown. FIG. 6 shows an orientation of toggle mechanism 90 when sample collection tank 88 is not installed in hollow guide 87 of sample tank receptacle 86, where spring 128 is positioned beyond the 12 o'clock position in a clockwise direction in the orientation as shown, thus defining a home position 133 for toggle mechanism 90.

FIG. 7 shows an orientation of toggle mechanism 90 when sample collection tank 88 is installed (inserted) in hollow guide 87 of sample tank receptacle 86. As sample collection tank 88 is inserted in hollow guide 87 of sample tank receptacle 86, rack gear 124 of sample collection tank 88 engages rotary gear 126 and rotates rotary gear 126 about rotational axis 130 in the counterclockwise direction in the orientation as shown. When spring 128 is moved beyond break-over point 132, e.g., the 12 o'clock position, in the counterclockwise direction as sample collection tank 88 is slidably received by sample tank receptacle 86, spring 128 provides a biasing force 134, e.g., a downward pressure, via rotary gear 126 to bias sample collection tank 88 downwardly toward longitudinal axis 445. Thus, biasing force 134 exerts downward pressure on sample collection tank 88 when spring 128 is moved beyond the 12 o'clock position in the counterclockwise direction, in the orientation as shown in FIG. 7, and biasing force 134 is maintained when sample collection tank 88 is installed in sample tank receptacle 86.

Figure 9:
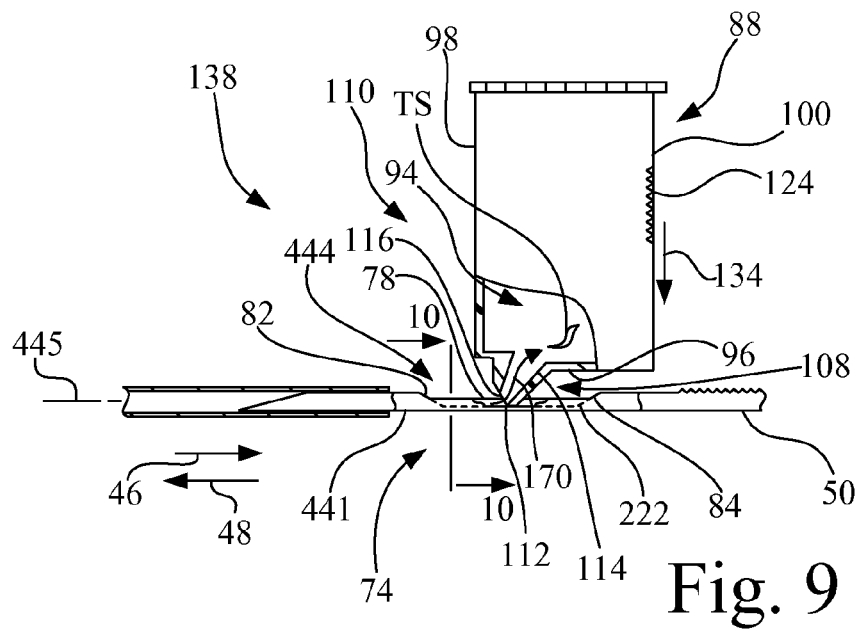
FIG. 9 is a side view of a portion of the tissue sample retrieval mechanism of FIG. 8 with a portion of the cutter cannula sectioned away to expose the retracting sample basket, and with a portion of the sample basket broken way to show the interaction of the tissue sample scoop of the sample collection tank with the sample notch.
Figure 11:
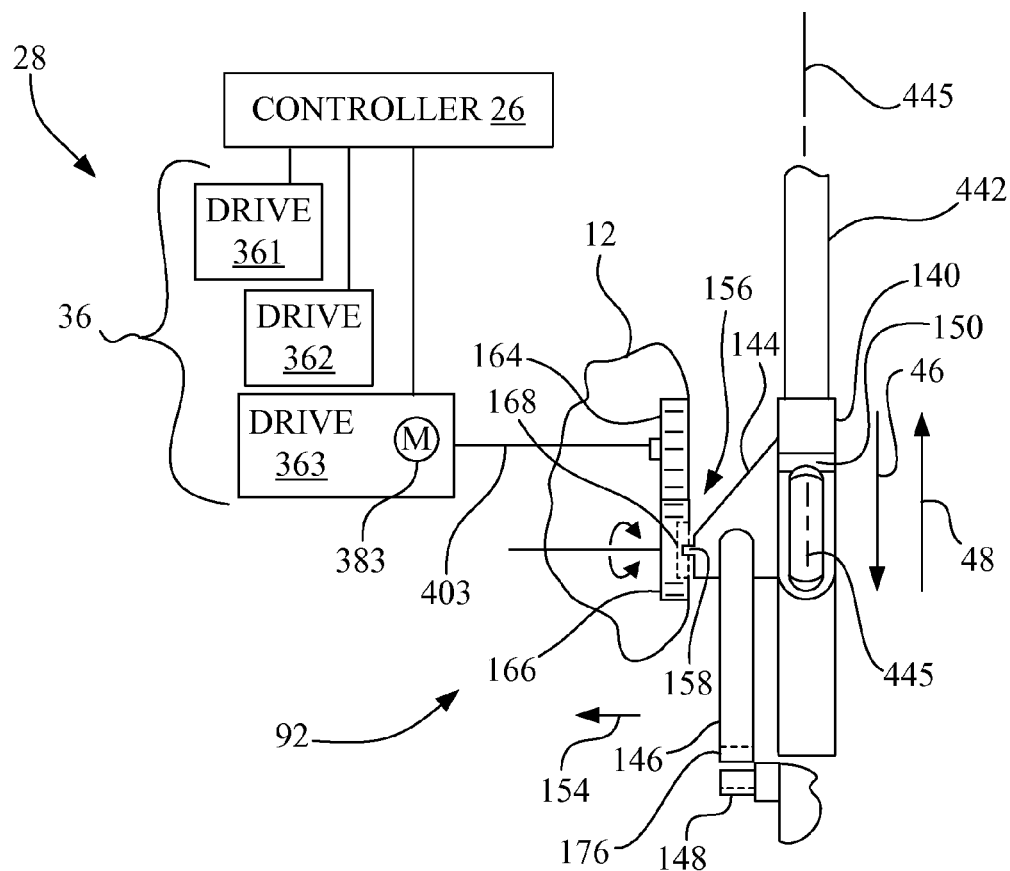
FIG. 11 is a top view of the tank positioning mechanism of FIG. 8.
Figure 10:
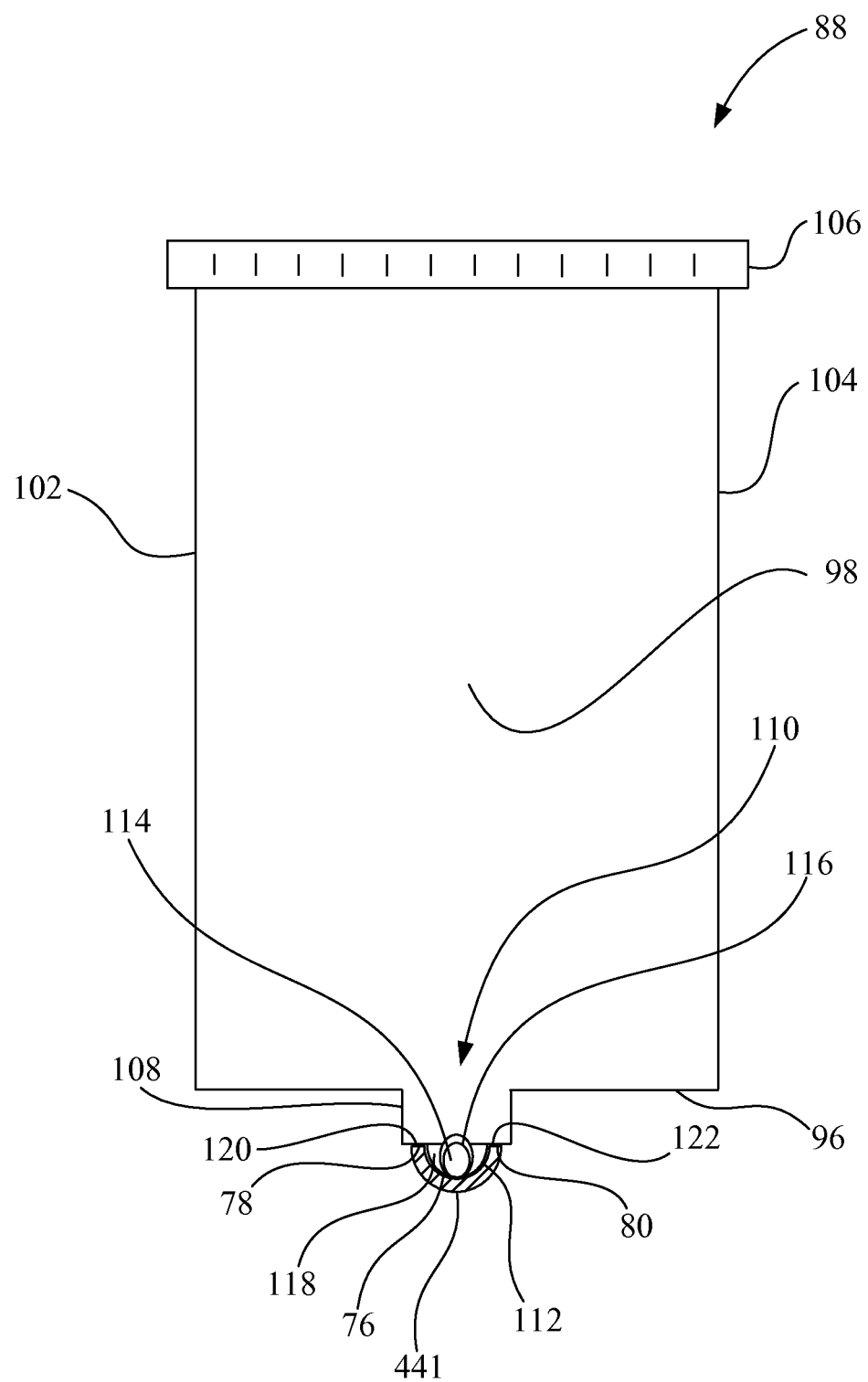
FIG. 10 is an enlarged front view of the sample collection tank of FIG. 9 showing the interaction of the rim of the sample collection tank with the sample basket shown in section along line 10-10 of FIG. 9.

Referring to FIG. 11 in conjunction with FIGS. 7-9, tank positioning mechanism 92 is configured to selectively move sample collection tank 88 between a raised position 136 illustrated in FIG. 7 and a lowered position 138 illustrated in FIGS. 8 and 9.

Tank positioning mechanism 92 is drivably engaged with electromechanical power source 28 to selectively lower, in conjunction with toggle mechanism 90, sample collection tank 88 from raised position 136 to lowered position 138 to position a portion, i.e., tissue sample scoop 108, of sample collection tank 88 in sliding engagement with sample notch 444 to facilitate collection of a tissue sample, e.g., tissue sample TS, from sample basket 441 as sample basket 441 is moved in tissue sample retrieval region 74. Also, electromechanical power source 28 is drivably engaged with tank positioning mechanism 92 and/or flexible toothed rack 50 to selectively raise sample collection tank 88, against the biasing force 134 exerted by toggle mechanism 90 and the biasing force 152 exerted by tank positioning mechanism 92, from lowered position 138 to raised position 136 to disengage sample collection tank 88 from sample notch 444 of sample basket 441 prior to, and following, tissue collection from sample basket 441.

More particularly, referring to FIGS. 6-8 and 11, tank positioning mechanism 92 includes a lift member 140, a spring 142, a lever 144, a latch member 146 and a latch catch 148.

Referring to FIGS. 7 and 8, lift member 140 is positioned along longitudinal axis 445. Lift member 140 has a ramp surface 150 positioned to engage ramped face 118 of sample collection tank 88. Spring 142 is positioned between lift member 140 and housing 57 to exert biasing force 152 on lift member 140 to bias ramp surface 150 in a direction away from ramped face 118 of sample collection tank 88.

As shown in FIG. 11, lever 144 extends from lift member 140 in a direction 154 perpendicular to longitudinal axis 445. Lever 144 has a distal end 156 configured to engage electromechanical power source 28, which may be in the form of a pin 158.

Electromechanical power source 28 is operable to move lift member 140 along longitudinal axis 445 in direction 46 to lift sample collection tank 88 away from longitudinal axis 445 as ramp surface 150 of lift member 140 slides along ramped face 118 of sample collection tank 88. Likewise, electromechanical power source 28 is operable to move lift member 140 along longitudinal axis 445 in direction 48 opposite direction 46 to lower sample collection tank 88 toward longitudinal axis 445 as ramp surface 150 of lift member 140 slides along ramped face 118 of sample collection tank 88.

As shown in FIG. 11, electromechanical power source 28 includes a lift drive 363 having an electrical motor 383 coupled to a motion transfer unit 403 (shown schematically in part by a line) that generally terminates at gears 164 and 166. Gear 166 includes a slot 168 for engaging pin 158 of lever 144. Motion transfer unit 403 provides rotary motion to gear 164, which in turn imparts rotary motion to gear 166. Motion transfer unit 403 may include one or more of a gear, gear train, belt/pulley arrangement, etc., for effecting at least a partial rotation of gear 164. Gear 166, however, is only rotated at a partial revolution, so as to effect a linear translation of pin 158 of lever 144, and in turn a linear translation of lift member 140.

The lowering of sample collection tank 88 for tissue sample collection (retrieval) is initiated by electromechanical power source 28 wherein gear 166 of lift drive 363 of electromechanical power source 28 is rotated in a direction to translate the lever 144, and in turn lift member 140, in direction 48 to lower sample collection tank 88. Biasing force 152 exerted on lift member 140 aids in moving ramp surface 150 in direction 48 away from ramped face 118 of sample collection tank 88. At this time, first shoulder 120 and second shoulder 122 of tissue sample scoop 108 are positioned for respective sliding engagement with the pair of spaced elongate edges 78, 80 of the elongate recessed region of sample notch 444 of sample basket 441 along longitudinal axis 445.

More particularly, with reference to FIGS. 8 and 11, the translation of the lever 144 and in turn lift member 140 in direction 48 causes the oblique face ramped face 118 of sample collection tank 88 to slide down the oblique ramp surface 150 of lift member 140, and tissue sample scoop 108 with rim 112 are moved into the elongate recessed region of sample notch 444 of sample basket 441 toward recessed floor 76. Referring also to FIGS. 9 and 10, continued transport of the sample notch 444 in direction 46 by electromechanical power source 28 will cause rim 112 of tissue sample scoop 108 to slide along recessed floor 76 and along the sides between elongate edges 78, 80 of sample notch 444, scooping up the tissue sample TS and transporting the tissue sample TS through tissue collection lumen 114 into collection cavity 94 of sample collection tank 88 along path 170. The shoulders 120, 122 of sample collection tank 88 are configured to slide along the upper spaced elongate edges 78, 80 of sample basket 441, ensuring that no tissue sample material is pushed out of sample notch 444.

The raising of sample collection tank 88 occurs near the conclusion of the tissue collection sequence. Near the conclusion of the tissue collection sequence, the further movement of sample notch 444 of sample basket 441 in direction 46 by operation of electromechanical power source 28 and second drive 362 is transferred to lift member 140 by a driving engagement of sample basket 441 in direction 46 with a T-shaped stop 172 (see FIG. 12) attached to lift member 140, causing lift member 140 to move in direction 46. The scoop rim 112 of sample collection tank 88 reaches the sloping leading transition bevel 82 of sample notch 444 and is pushed upwards by the interplay between ramped face 118 of sample collection tank 88 and leading transition bevel 82 of sample notch 444, thus beginning to raise sample collection tank 88. As lift member 140 is further moved in direction 46 by movement of sample notch 444, the scoop rim 112 leaves sample notch 444 and ramped face 118 of sample collection tank 88 and comes to rest against ramp surface 150 of lift member 140, which closes off tissue collection lumen 114 of sample collection tank 88 and prevents the tissue sample TS from falling out of tissue collection lumen 114.

In addition, lift drive 363 is rotated to ensure that lift member 140 is translated fully in direction 46 in the event that the force exerted by sample notch 444 is insufficient to accomplish the translation. More particularly, electromechanical power source 28 rotates gear 166 of lift drive 363 in a direction to translate the lever 144 in direction 46. Thus, electromechanical power source 28 facilitates movement of lift member 140 along longitudinal axis 445 in first direction 46 against the biasing force 152 exerted by spring 142 to lift sample collection tank 88 as ramp surface 150 of lift member 140 slides along ramped face 118 of sample collection tank 88.

At the conclusion of the transport of sample notch 444 in direction 46 towards the proximal end of driver assembly 12, a leaf spring tongue 174 of T-shaped stop 172 (see FIG. 12) removes residual tissue material and debris from the second end 222 of vacuum path 22 at trailing transition bevel 84 of sample notch 444 to ensure that a sufficient vacuum may be drawn into sample notch 444.

Referring again to FIGS. 6-8, 11 and 13, latch member 146 is attached to, or formed integral with, lift member 140. Latch member 146 extends from lever 144 in direction 46, and has a distal hook 176. Latch member 146 is located for engagement with latch catch 148 to latch lift member 140 in a transport latched position, shown in FIG. 13, corresponding to raised position 136 of sample collection tank 88. Latch catch 148 may be attached to, or formed integral with, housing 57.

Figure 13:
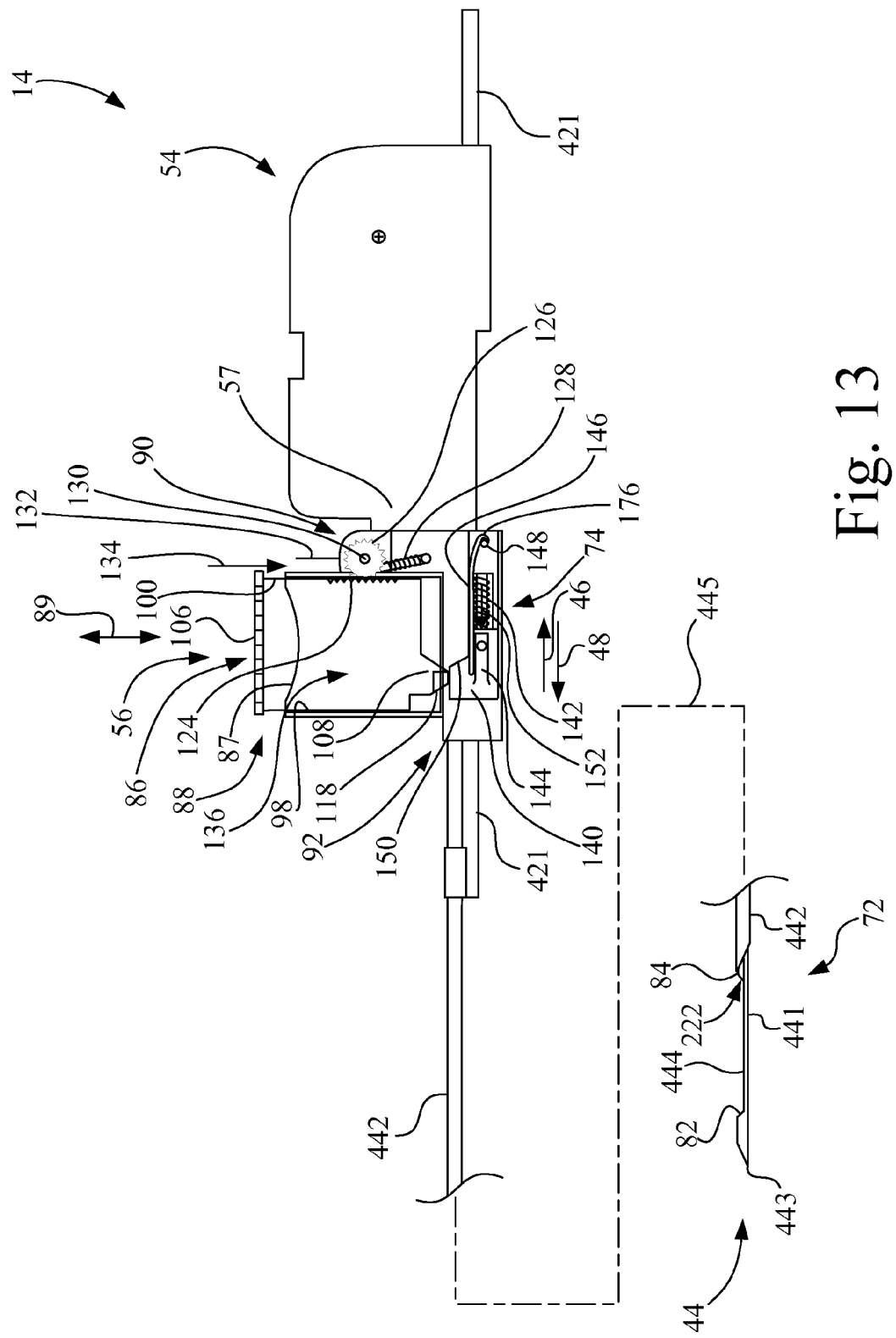
FIG. 13 is a side view of the disposable biopsy probe of FIG. 7 showing the latch member of the tank positioning mechanism in the latched transport position.

One purpose of latch member 146 is to maintain the proper insertion position of lever 144 during transport of biopsy probe assembly 14 to ensure proper insertion of biopsy probe assembly 14 in driver assembly 12. Prior to insertion of biopsy probe assembly 14 in driver assembly 12, lever 144 is held in a latched transport position, which is the only position permitting pin 158 at distal end 156 of lever 144 to be inserted into slot 168 (e.g., a driver recess) of lift drive 363 (see FIG. 11). In the latched transport position, as illustrated in FIG. 13, the lever 144 is held in position by latch member 146 that is held in tension against latch catch 148 by pressure (biasing force 152) from spring 142. Thus, insertion of biopsy probe assembly 14 in driver assembly 12 in the latched transport position results in placement of pin 158 at distal end 156 of lever 144 in slot 168 (e.g., a driver recess) of lift drive 363.

A second purpose of the latch member 146 is to prevent accidental reuse of the disposable probe. As part of power up, the lift drive 363 engages pin 158 at distal end 156 of lever 144 and moves lever 144 in direction 46 to a fully retracted position, which in turn causes latch member 146 to move out of engagement with latch catch 148. The tension of the latch member 146 is released, causing latch member 146 to move out of the plane of latch catch 148 and preventing latch member 146 from reestablishing contact with latch catch 148. Since spring 142 will bias lift member 140 in direction 48, the latched transport position illustrated in FIG. 13 may not be reestablished once biopsy probe assembly 14 has been removed from driver assembly 12. Since the latched transport position is the only position permitting biopsy probe assembly 14 to be inserted in driver assembly 12, accidental reuse of biopsy probe assembly 14 is prevented.

Figure 14:
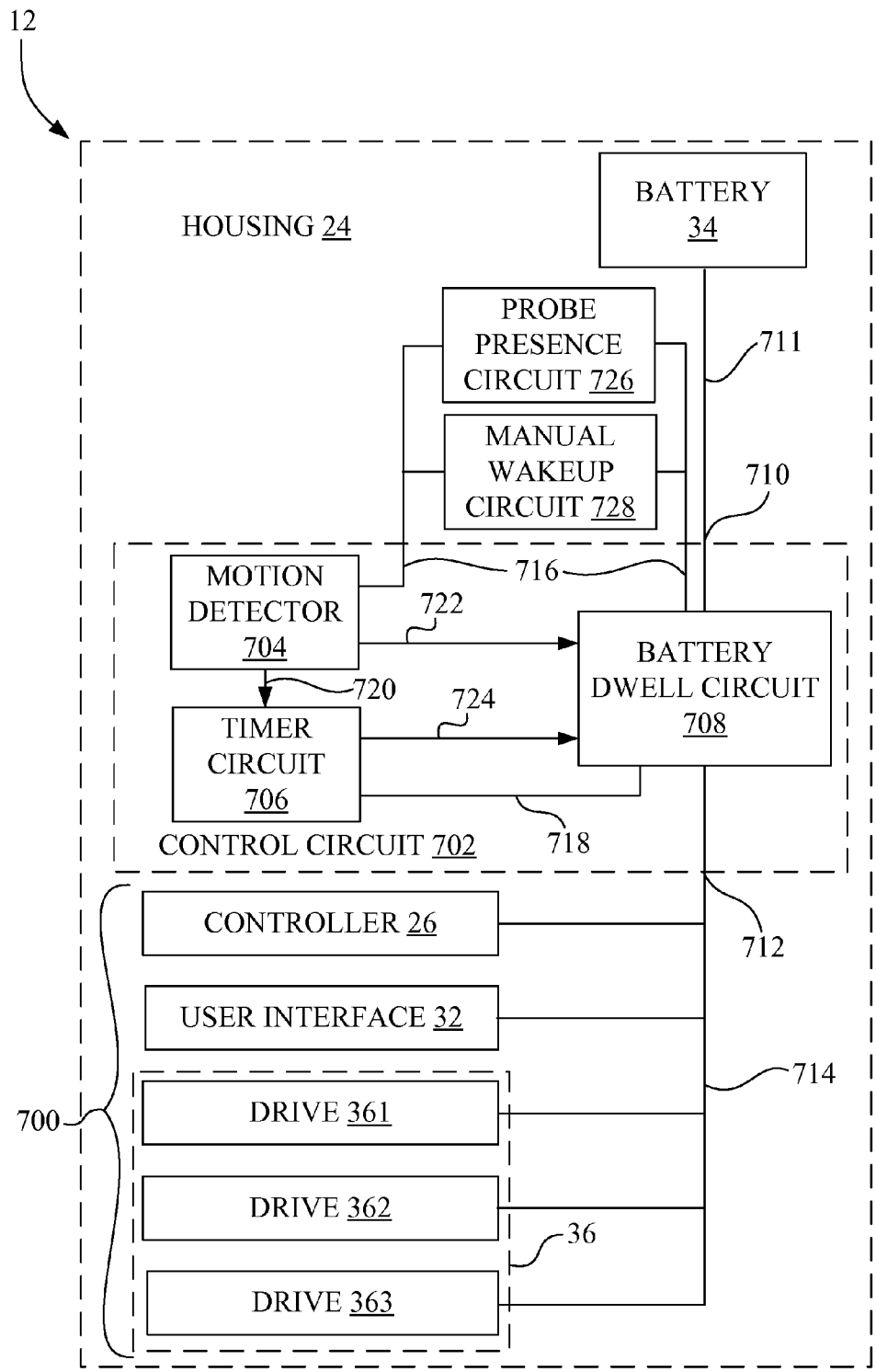
FIG. 14 is a block diagram of a circuit for conserving battery power in the biopsy driver assembly of FIGS. 1.
Figure 15:
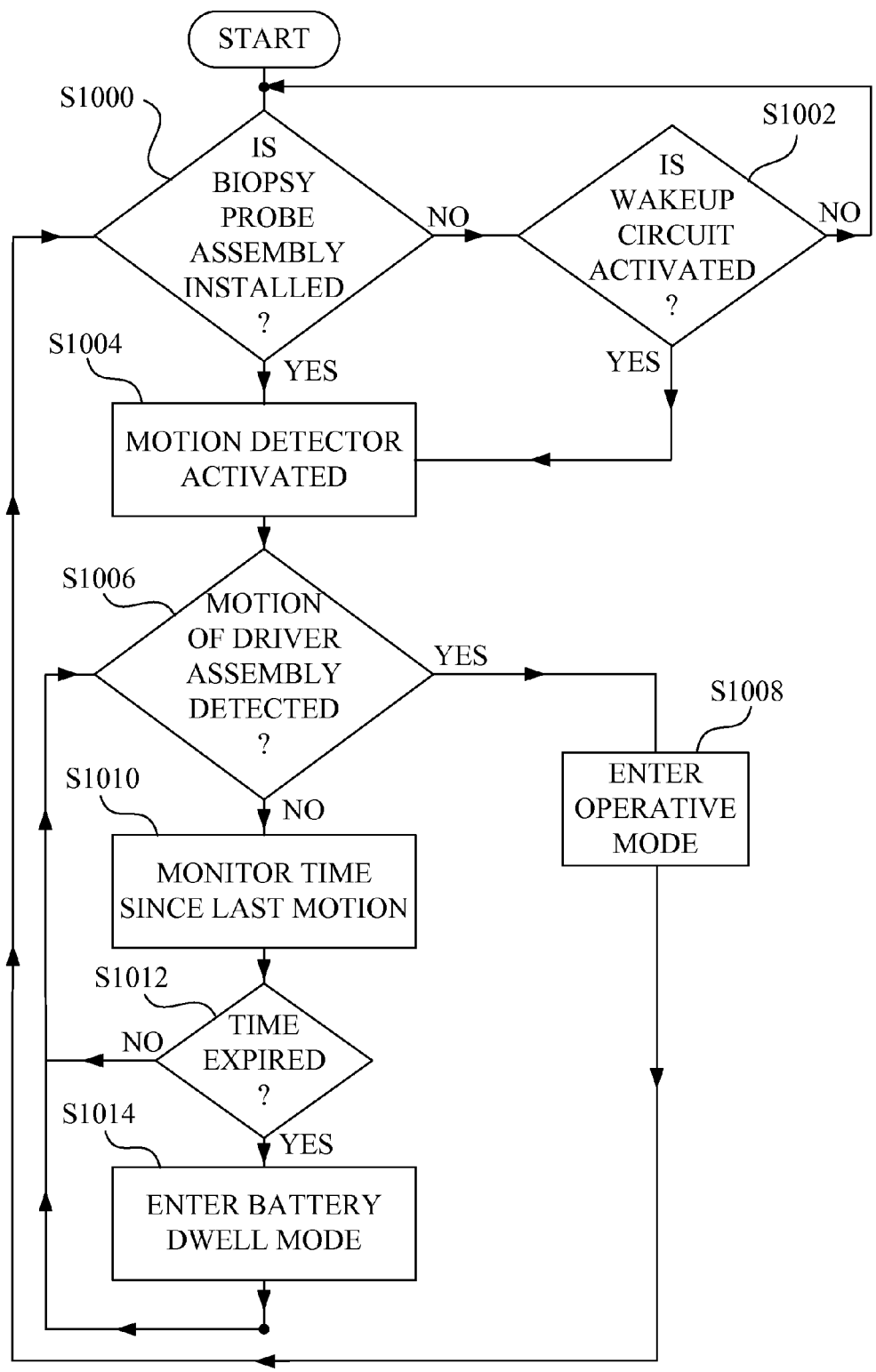
FIG. 15 is a flowchart of a process for conserving battery power in accordance with the embodiment shown in FIG. 14.

Referring to FIGS. 14 and 15, the present invention provides circuitry to prolong the life of battery 34, and thus aid in preventing malfunctions due to lack of battery power.

Referring to FIG. 14, biopsy driver assembly 12 includes an electrical assembly 700. In the present exemplary embodiment, electrical assembly 700 includes, but is not limited to, the previously described components of controller 26, user interface 32, electrical drive 361, electrical drive 362, and electrical drive 363. Electrical assembly 700 is coupled to, e.g., mounted within in substantial part, biopsy driver housing 24. As previously described, each of the electrical drives 361, 362, and 363 is configured to drivably engage corresponding driven units 421, 422 and tank positioning mechanism 92, respectively, of biopsy probe assembly 14.

In accordance with an aspect of the present invention, a control circuit 702 is coupled to, and contained in, biopsy driver housing 24 of biopsy driver assembly 12. Control circuit 702 is electrically coupled to battery 34 and to electrical assembly 700. Control circuit 702 includes a motion detector 704, a timer circuit 706, and a battery dwell circuit 708.

Control circuit 702 is configured, using digital logic and electrical power components, to conserve battery 34 by providing electrical power only to motion detector 704 after a predetermined time following a last detected physical movement of biopsy driver assembly 12. For example, in the present example, control circuit may be configured to turn off electrical power to electrical assembly 700 and to timer circuit 706 after a predetermined time following the last detected physical movement of biopsy driver assembly 12, while maintaining electrical power to motion detector 704. Further, control circuit 702 is configured to provide electrical power from battery 34 to all electrical components of biopsy driver assembly 12, including electrical assembly 700, when a physical movement of biopsy driver assembly 12 is detected.

Battery dwell circuit 708 has a power input 710 electrically connected via power link 711 to battery 34, and has a power output 712 electrically connected to controller 26, user interface 32, and electrical assembly 700, e.g., via a power bus 714. Motion detector 704 is electrically connected via electrical power link 716 to receive electrical power from battery dwell circuit 708. Timer circuit 706 is electrically connected via electrical power link 718 to receive electrical power from battery dwell circuit 708. Each of electrical power links 711, 716 and 718, and power bus 714 may be, for example, a wired connection, such as a printed circuit or wire cabling, and may include intervening components, such as switches and power electronic components.

Motion detector 704 is communicatively coupled via communication link 720 to timer circuit 706. Motion detector 704 is communicatively coupled via communication link 722 to battery dwell circuit 708. Timer circuit 706 is communicatively coupled via communication link 724 to battery dwell circuit 708. Each of communication links 720, 722, and 724 may be, for example, a wired link, such as a printed circuit or wire cabling.

Motion detector 704 is configured, e.g., through electronic hardware, firmware and/or software, to provide a first signal via communication link 722 to battery dwell circuit 708 to cause battery dwell circuit 708 to enter an operative mode. In the operative mode, electrical power is supplied to electrical assembly 700 when physical movement of biopsy driver assembly 12 is detected by motion detector 704.

Also, motion detector 704 is configured to provide a second signal via communication link 720 to timer circuit 706. The second signal provided by motion detector 704 to timer circuit 706 indicates the occurrence of the last detected physical movement of biopsy driver assembly 12 that was detected by motion detector 704.

Timer circuit 706 is configured, e.g., through electronic hardware, firmware and/or software, to perform a timer function, and to provide a third signal via communication link 724 to battery dwell circuit 708. More particularly, when timer circuit 706 receives the second signal from motion detector 704, time circuit begins monitoring the time since the last physical movement of biopsy driver assembly 12. When a predetermined time, e.g. time threshold, is reached, timer circuit 706 provides the third signal to battery dwell circuit 708. The third signal provided by timer circuit 706 causes battery dwell circuit 708 to enter a battery dwell mode. In the battery dwell mode, electrical power is supplied to motion detector 704 to the exclusion of timer circuit 706 and electrical assembly 700, e.g., only to motion detection 704. The third signal is supplied to battery dwell circuit 708 after the predetermined time following the last detected physical movement of biopsy driver assembly 12.

The length of the predetermined time measured by timer circuit 706 may be selected, for example, as a time of sufficient length to prevent constant cycling of electrical assembly 700 ON and OFF, while being short enough to provide the desired power consumption reduction from battery 34. In the present embodiment, for example, the predetermined time is selected to be two minutes.

In accordance with another aspect of the invention, in order to avoid unnecessary powering of motion detector 704, timer circuit 706, and electrical assembly 700 during the transport/shipping of biopsy driver assembly 12, a probe presence circuit 726 is electrically coupled into electrical power link 716 between battery dwell circuit 708 and motion detector 704. Probe presence circuit 726 is configured, e.g., through electronic hardware, firmware and/or software, to detect a mounting of biopsy probe assembly 14 to biopsy driver assembly 12. More particularly, probe presence circuit 726 is configured to de-activate, i.e., not power up, motion detector 704 if biopsy probe assembly 14 is not mounted to biopsy driver assembly 12, such that neither the operative mode nor the battery dwell mode is operational if the biopsy probe assembly 14 is not mounted to biopsy driver assembly 12. In its simplest form, probe presence circuit 726 may be a contact switch electronically interposed in electrical power link 716.

However, it is contemplated that at times it may be desired to check the functioning of biopsy driver assembly 12 without biopsy probe assembly 14 being mounted to biopsy driver assembly 12. Accordingly, as another aspect of the invention, a manual wakeup circuit 728 is electrically coupled into electrical power link 716 between battery dwell circuit 708 and motion detector 704, e.g., in parallel with probe presence circuit 726. Manual wakeup circuit 728 is configured, e.g., through electronic hardware, firmware and/or software, to bypass probe presence circuit 726 to activate (e.g., power up) motion detector 704 when manual wakeup circuit 728 is actuated by a user to cause battery dwell circuit 708 to enter the operative mode in an absence of biopsy probe assembly 14 being mounted to biopsy driver assembly 12. In its simplest form, manual wakeup circuit 728 may be a switch electronically interposed in electrical power link 716, in parallel with probe presence circuit 726.

FIG. 15 is a flowchart of a process for conserving battery power in accordance with the embodiment shown in FIG. 14.

At act S1000, it is determined whether biopsy probe assembly 14 is installed on biopsy driver assembly 12, which is the function of probe presence circuit 726.

If the determination at act S1000, is NO, the process proceeds to act S1002 to determine whether the manual wakeup circuit 728 has been actuated. If the determination at act S1002 is NO, the process returns to act S1000. However, if the determination at act S1002 is YES, then the process proceeds to act S1004, wherein motion detector 704 is activated, i.e., powered up.

Likewise, if the determination at act S1000 is YES, then the process proceeds to act S1004, wherein motion detector 704 is activated, i.e., powered up.

At act S1006, it is determined whether physical movement of biopsy driver assembly 12 is occurring, as detected by motion detector 704. If the determination is YES, then at act S1008 battery dwell circuit 708 enters the operative mode, wherein electrical power is supplied to electrical assembly 700, and the process returns to act S1000 to continue monitoring.

If, at act S1006, the determination is NO, then at act S1010 timer circuit 706 is actuated to monitor the time since the last physical movement of biopsy driver assembly 12.

At act S1012, it is determined whether the predetermined time, e.g., two minutes, since the last physical movement of biopsy driver assembly 12 has expired.

If the determination at act S1012 is NO, i.e., that the predetermined time has not expired, then the process continues at act S1006, e.g., while remaining in the operative mode.

If the determination at act S1012 is YES, i.e., that the predetermined time has expired, then at act S1014 battery dwell circuit 708 enters the battery dwell mode wherein electrical power is supplied only to motion detector 704, and, wherein motion monitoring continues at act S1006, while remaining in the battery dwell mode.

Thus, in accordance with aspects of the present invention, biopsy driver assembly 12 may be mounted to, and operated in conjunction with, biopsy probe assembly 14 in prolonged sessions, while keeping power consumption to a reasonable minimum to prolong the life of battery 34 and aid in preventing malfunctions of biopsy apparatus 10 due to lack of battery power.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A biopsy driver assembly configured to mount a biopsy probe assembly, comprising:
 a biopsy driver housing;
 an electrical assembly coupled to said biopsy driver housing, said electrical assembly including at least one electrical drive configured for drivably engaging said biopsy probe assembly;
 a battery coupled to said biopsy driver housing;
 a control circuit coupled to said biopsy driver housing, said control circuit being electrically coupled to said battery and to said electrical assembly, said control circuit having a motion detector, a timer circuit and a battery dwell circuit, said control circuit being configured to conserve said battery by providing electrical power to said motion detector to the exclusion of said timer circuit and said electrical assembly after a predetermined time following a last detected physical movement of said biopsy driver assembly and to provide electrical power from said battery also to said timer circuit and said electrical assembly when a physical movement of said biopsy driver assembly is detected;
 said battery dwell circuit has a power input electrically connected to said battery and a power output electrically connected to said electrical assembly;
 each of said motion detector and said timer circuit is electrically connected to receive electrical power from said battery dwell circuit;
 said motion detector is communicatively coupled to said timer circuit via a first communication link and to said dwell circuit via a second communication link, said motion detector being configured to provide a first signal to said battery dwell circuit to cause said battery dwell circuit to enter an operative mode wherein electrical power is supplied to said electrical assembly when said physical movement of said biopsy driver assembly is detected, and said motion detector being configured to provide a second signal to said timer circuit that indicates said last detected physical movement of said biopsy driver assembly;
 said timer circuit is communicatively coupled to said battery dwell circuit via a third communication link, said timer circuit being configured to provide a third signal to said battery dwell circuit to cause said battery dwell circuit to enter a battery dwell mode wherein electrical power is supplied to said motion detector to the exclusion of said timer circuit and said electrical assembly, said third signal being supplied to said battery dwell circuit after said predetermined time following said last detected physical movement of said biopsy driver assembly;
 a probe presence circuit electrically coupled to said battery dwell circuit and to said motion detector, said probe presence circuit being configured to detect a mounting of said biopsy probe assembly to said biopsy driver assembly, said probe presence circuit being configured to de-activate said motion detector if said biopsy probe assembly is not mounted to said biopsy driver assembly such that neither said operative mode nor said battery dwell mode is operational; and
 a manual wakeup circuit electrically coupled to said battery dwell circuit and to said motion detector, said manual wakeup circuit being configured to bypass said probe presence circuit to activate said motion detector when said manual wakeup circuit is actuated by a user to cause said battery dwell circuit to enter said operative mode in an absence of said biopsy probe assembly being mounted to said biopsy driver assembly.

2. A biopsy apparatus, comprising:
 a biopsy probe assembly having a sample basket arranged coaxially with a cutter cannula relative to a longitudinal axis, and having a first driven unit coupled to said cutter cannula to facilitate movement of said cutter cannula relative to said longitudinal axis, and having a second driven unit coupled to said sample basket to facilitate movement of said sample basket relative to said longitudinal axis; and a biopsy driver assembly configured to mount said biopsy probe assembly, said biopsy driver assembly including:

a biopsy driver housing;

an electrical assembly coupled to said biopsy driver housing, said electrical assembly including a first electrical drive configured for drivably engaging said first driven unit of said biopsy probe assembly and a second electrical drive configured for drivably engaging said second driven unit of said biopsy probe assembly;

a battery coupled to said biopsy driver housing;

a control circuit coupled to said biopsy driver housing, said control circuit being electrically coupled to said battery and to said electrical assembly, said control circuit having a motion detector, a timer circuit and a battery dwell circuit, said control circuit being configured to conserve said battery by providing electrical power to said motion detector to the exclusion of said timer circuit and said electrical assembly after a predetermined time following a last detected physical movement of said biopsy driver assembly and to provide electrical power from said battery also to said timer circuit and said electrical assembly when a physical movement of said biopsy driver assembly is detected;

said battery dwell circuit has a power input electrically connected to said battery and a power output electrically connected to said electrical assembly;

each of said motion detector and said timer circuit is electrically connected to receive electrical power from said battery dwell circuit;

said motion detector is communicatively coupled to said timer circuit via a first communication link and to said dwell circuit via a second communication link, said motion detector being configured to provide a first signal to said battery dwell circuit to cause said battery dwell circuit to enter an operative mode wherein electrical power is supplied to said electrical assembly when said physical movement of said biopsy driver assembly is detected, and said motion detector being configured to provide a second signal to said timer circuit that indicates said last detected physical movement of said biopsy driver assembly;

said timer circuit is communicatively coupled to said battery dwell circuit via a third communication link, said timer circuit being configured to provide a third signal to said battery dwell circuit to cause said battery dwell circuit to enter a battery dwell mode wherein electrical power is supplied to said motion detector to the exclusion of said timer circuit and said electrical assembly, said third signal being supplied to said battery dwell circuit after said predetermined time following said last detected physical movement of said biopsy driver assembly;

a probe presence circuit electrically coupled to said battery dwell circuit and to said motion detector, said probe presence circuit being configured to detect a mounting of said biopsy probe assembly to said biopsy driver assembly, said probe presence circuit being configured to de-activate said motion detector if said biopsy probe assembly is not mounted to said biopsy driver assembly such that neither said operative mode nor said battery dwell mode is operational; and a manual wakeup circuit electrically coupled to said battery dwell circuit and to said motion detector, said manual wakeup circuit being configured to bypass said probe presence circuit to activate said motion detector when said manual wakeup circuit is actuated by a user to cause said battery dwell circuit to enter said operative mode in an absence of said biopsy probe assembly being mounted to said biopsy driver assembly.

\* \* \* \* \*